(12) United States Patent
Weiss et al.

(10) Patent No.: US 8,975,029 B2
(45) Date of Patent: Mar. 10, 2015

(54) INTEGRIN ALPHA-2 BINDING AGENTS AND USE THEREOF TO INHIBIT CANCER CELL PROLIFERATION

(75) Inventors: Stephen J. Weiss, Ann Arbor, MI (US); David T. Dudley, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 60 days.

(21) Appl. No.: 13/474,872

(22) Filed: May 18, 2012

(65) Prior Publication Data

US 2012/0294865 A1 Nov. 22, 2012

Related U.S. Application Data

(60) Provisional application No. 61/487,812, filed on May 19, 2011.

(51) Int. Cl.
| | | |
|---|---|---|
| G01N 33/53 | (2006.01) | |
| C07K 16/00 | (2006.01) | |
| C07K 16/46 | (2006.01) | |
| C07K 16/28 | (2006.01) | |
| A61K 39/00 | (2006.01) | |

(52) U.S. Cl.
CPC ......... *C07K 16/2842* (2013.01); *C07K 2317/34* (2013.01); *A61K 2039/505* (2013.01); *C07K 2317/73* (2013.01)
USPC ................... 435/7.1; 530/387.1; 530/388.22; 530/387.3

(58) Field of Classification Search
None
See application file for complete search history.

(56) References Cited

U.S. PATENT DOCUMENTS

| | | | |
|---|---|---|---|
| 4,331,647 A | 5/1982 | Goldenberg | |
| 4,816,567 A | 3/1989 | Cabilly et al. | |
| 5,139,941 A | 8/1992 | Muzyczka et al. | |
| 5,252,479 A | 10/1993 | Srivastava | |
| 5,328,688 A | 7/1994 | Roizman | |
| 5,399,363 A | 3/1995 | Liversidge et al. | |
| 5,466,468 A | 11/1995 | Schneider et al. | |
| 5,474,935 A | 12/1995 | Chatterjee et al. | |
| 5,585,362 A | 12/1996 | Wilson et al. | |
| 5,622,856 A | 4/1997 | Natsoulis | |
| 5,631,237 A | 5/1997 | Dzau et al. | |
| 5,658,776 A | 8/1997 | Flotte et al. | |
| 5,660,827 A | 8/1997 | Thorpe et al. | |
| 5,661,033 A | 8/1997 | Ho et al. | |
| 5,670,488 A | 9/1997 | Gregory et al. | |
| 5,693,509 A | 12/1997 | Cotten et al. | |
| 5,707,618 A | 1/1998 | Armentano et al. | |
| 5,712,120 A | 1/1998 | Rodriguez et al. | |
| 5,773,289 A | 6/1998 | Samulski et al. | |
| 5,789,390 A | 8/1998 | Descamps et al. | |
| 5,792,453 A | 8/1998 | Hammond et al. | |
| 5,824,544 A | 10/1998 | Armentano et al. | |
| 5,830,727 A | 11/1998 | Wang et al. | |
| 5,834,441 A | 11/1998 | Philip et al. | |
| 5,849,571 A | 12/1998 | Glorioso et al. | |
| 5,851,521 A | 12/1998 | Branellec et al. | |
| 5,855,888 A | 1/1999 | Nishida et al. | |
| 5,856,152 A | 1/1999 | Wilson et al. | |
| 5,859,205 A * | 1/1999 | Adair et al. | ................ 530/387.3 |
| 5,861,155 A | 1/1999 | Lin | |
| 5,863,541 A | 1/1999 | Samulski et al. | |
| 5,869,619 A | 2/1999 | Studnicka | |
| 5,877,397 A | 3/1999 | Lonberg et al. | |
| 5,879,934 A | 3/1999 | DeLuca | |
| 5,939,598 A | 8/1999 | Kucherlapati et al. | |
| 6,054,927 A | 4/2000 | Brickell | |
| 6,180,370 B1 | 1/2001 | Queen et al. | |

FOREIGN PATENT DOCUMENTS

| | | |
|---|---|---|
| WO | WO-94/02602 A1 | 2/1994 |
| WO | WO-96/33735 A1 | 10/1996 |
| WO | WO-9630498 A1 | 10/1996 |
| WO | WO-98/24893 A2 | 6/1998 |
| WO | WO-2006/022682 A2 | 3/2006 |
| WO | WO-2007/056858 A1 | 5/2007 |
| WO | WO-2010/052556 A1 | 5/2010 |

OTHER PUBLICATIONS

Hughes et al. Platelet integrin α2 I-domain specific antibodies produced via domain specific DNA vaccination combined with variable gene phage display. Thromb Haemost 2005; 94: 1318-26.*
Campbell A, General properties and applications of monoclonal antibodies, Elsevier Science Publishers, section 1.1, pp. 1-32, 1984.*
Klimka et al.,Human anti-CD30 recombinant antibodies by guided phage antibody selection using cell panning. British Journal of Cancer (2000) 83:252-260.*
Rudikoff et al Single amino acid substitution altering antigen-binding specificity. Proc Natl Acad Sci U S A. Mar. 1982;79(6):1979-83.*
Beiboer et al., Guided selection of a pan carcinoma specific antibody reveals similar binding characteristics yet structural divergence between the original murine antibody and its human equivalent. J. Mol. Biol. 296: 833-849 (2000).*
Brown et al. Tolerance of single, but not multiple, amino acid replacements in antibody VH CDR 2: a means of minimizing B cell wastage from somatic hypermutation? J. Immuno. May 1996, 3285-91.*
Vajdos et al. Comprehensive functional maps of the antigen-binding site of an anti-ErbB2 antibody obtained with shotgun scanning mutagenesis. J. Mol. Biol. Jul. 5, 2002, 320(2):415-28.*
Eduardo Padlan, Anatomy of the antibody molecule. Mol Immunol. Feb. 1994;31(3):169-217.*
Paul, Fundamental Immunology, 3rd Edition, 1993, pp. 292-295.*
Bendayan M. Possibilities of false immunocytochemical results generated by the use of monoclonal antibodies: the example of the anti-proinsulin antibody. J Histochem Cytochem. 43(9):881-6, 1995.*

(Continued)

*Primary Examiner* — Maher Haddad
(74) *Attorney, Agent, or Firm* — Marshall, Gerstein & Borun LLP

(57) ABSTRACT

The invention provides an integrin alpha-2 binding agent and methods of using an integrin alpha-2 binding agent to, e.g., inhibit proliferation of cancer cells, modulate tumor growth in a subject, inhibiting angiogenesis, or treating a fibrotic disorder. The invention further provides a method of producing an antibody, the method comprising propagating cancer cells in a 3-dimensional matrix; immunizing a mammal with the propagated cancer cells; and isolating an antibody from the immunized mammal. A method of identifying an agent that inhibits cancer cell proliferation also is provided.

10 Claims, No Drawings

(56) References Cited

OTHER PUBLICATIONS

Bost KL, Pascual DW. Antibodies against a peptide sequence within the HIV envelope protein crossreacts with human interleukin-2. Immunol Invest. 17(6-7):577-86, 1988.*

Van Regenmortel MHV. Mapping Epitope Structure and Activity: From One-Dimensional Prediction to Four-Dimensional Description of Antigenic Specificity Methods. 9(3):465-72, 1996.*

Girgert et al., Integrin I+-2- dificient mice provide insights into specific finctions of collogen receptors in the kidney, *Biomed.* 3(1):19 (2010).

Lu et al., The role of integrins in cancer and the development of anti-integrin therapeautic agents for cancer theraphy, *Per. Med. Chem.* 2:57-73 (2008).

Senger et al., The alpha(1) beta(1) and alpha(2) beta(1) integrinsprovide critical support for vasuclar endothelial growth factor signaling, endothelial cell migration, and tumor angiogenesis, *Amer. J. Path.* 160(1):195-204 (2004).

Tuckwell et al., Monoclonal antibodies idenitfy residues 199-216 of the integrin alpha2 vWFA domain as a functionally important region within alhpa2beta1, *Biochem. J.* 350: 485-93 (2000).

International search report and written opinion of the international searching authority, European Patent Office, dated Nov. 26, 2012.

Aiello et al., Suppression of retinal neovascularization in vivo by inhibition of vascular endothelial growth factor (VEGF) using soluble VEGF-receptor chimeric proteins. *Proc. Natl. Acad. Sci. U.S.A.*, 92(23):10457-61 (1995).

Alrefai et al., Molecular cloning and promoter analysis of downregulated in adenoma (DRA). *Am. J. Physiol. Gastrointest. Liver Physiol.*, 293(5):G923-34 (2007).

Benassi et al., Adhesion molecules in high-grade soft tissue sarcomas: correlation to clinical outcome. *Eur. J. Cancer*, 34(4):496-502 (1998).

Boshart et al., A very strong enhancer is located upstream of an immediate early gene of human cytomegalovirus. *Cell*, 41(2):521-30 (1985).

Bruggemann et al., Production of human antibody repertoires in transgenic mice. *Curr. Opin. Biotechnol.*, 8(4):455-8 (1997).

Canon et al., Inhibition of RANKL blocks skeletal tumor progression and improves survival in a mouse model of breast cancer bone metastasis. *Clin. Exp. Metastasis*, 25(2):119-29 (2008).

Canon et al., Inhibition of RANKL increases the anti-tumor effect of the EGFR inhibitor panitumumab in a murine model of bone metastasis. *Bone*, 46(6):1613-9 (2010).

Chen et al., High-efficiency transformation of mammalian cells by plasmid DNA. *Mol. Cell Biol.*, 7(8):2745-52 (1987).

Chen et al., The alpha(2) integrin subunit-deficient mouse: a multi-faceted phenotype including defects of branching morphogenesis and hemostasis. *Am. J. Pathol.*, 161(1):337-44 (2002).

Chiu et al., Involvement of AdipoR receptor in adiponectin-induced motility and alpha2beta1 integrin upregulation in human chondrosarcoma cells. *Carcinogenesis*, 30(10):1651-9 (2009).

Choi et al., Small molecule inhibitors of integrin alpha2beta1. *J. Med. Chem.*, 50(22):5457-62 (2007).

Clark, Antibody humanization: a case of the 'Emperor's new clothes'? *Immunol. Today*, 21(8):397-402 (2000).

Conn et al., Comparative analysis of metastasis variants derived from human prostate carcinoma cells: roles in intravasation of VEGF-mediated angiogenesis and Upa-mediated invasion. Am. J. Pathol., 175(4):1638-52 (2009).

Cuff et al., The human monocarboxylate transporter MCT1: gene structure and regulation. *Am. J. Physiol. Gastrointest. Liver Physiol.*, 289(5):G977 (2005).

Dall'acqua et al., Antibody humanization by framework shuffling. *Methods*, 36(1):43-60 (2005).

Davis et al., Direct gene transfer into skeletal muscle in vivo: factors affecting efficiency of transfer and stability of expression. *Hum. Gene Ther.*, 4(2):151-9 (1993).

Desgrosellier et al., Integrins in cancer: biological implications and therapeutic opportunities. *Nat. Rev. Cancer*, 10(1):9-22 (2010).

Dhar et al., Platelet-activating factor stimulation of tyrosine kinase and its relationship to phospholipase C in rabbit platelets: studies with genistein and monoclonal antibody to phosphotyrosine. *Mol. Pharmacol.*, 37(4):519-25 (1990).

Fechheimer et al., Transfection of mammalian cells with plasmid DNA by scrape loading and sonication loading. *Proc. Natl. Acad. Sci. U.S.A.*, 84(23):8463-7 (1987).

Felgner, Improvements in cationic liposomes for in vivo gene transfer. *Hum. Gene Ther.*, 7(15):1791-3 (1996).

Felgner, Nonviral strategies for gene therapy. *Sci. Am.*, 276(6):102-6 (1997).

Fishman et al., Metastatic dissemination of human ovarian epithelial carcinoma is promoted by alpha2beta1-integrin-mediated interaction with type I collagen. *Invasion Metastasis*, 18(1):15-26 (1998).

Fraley et al., Entrapment of a bacterial plasmid in phospholipid vesicles: potential for gene transfer. *Proc. Natl. Acad. Sci. U.S.A.*, 76(7):3348-52 (1979).

Frank et al, Microcirculation research, angiogenesis, and microsurgery. *Microsurgery*, 15(6):399-404 (1994).

Funahashi et al., Sulfonamide derivative, E7820, is a unique angiogenesis inhibitor suppressing an expression of integrin alpha2 subunit on endothelium. *Cancer Res.*, 62(21):6116-23 (2002).

Girotti et al., SPARC promotes cathepsin B-mediated melanoma invasiveness through a collagen I/$\alpha 2\beta 1$ integrin axis. *J. Invest. Dermatol.*, 131 (12):2438-47 (2011).

Gonzalez et al., An immunohistochemical examination of the expression of E-cadherin, alpha- and beta/gamma-catenins, and alpha2- and beta1 -integrins in invasive breast cancer. *J. Pathol.*, 187(5):523-9 (1999).

Gopal, Gene transfer method for transient gene expression, stable transformation, and cotransformation of suspension cell cultures. Mol. Cell Biol., 5(5):1188-90 (1985).

Graham et al., A new technique for the assay of infectivity of human adenovirus 5 DNA. Virology, 52(2):456-67 (1973).

Green et al., Antigen-specific human monoclonal antibodies from mice engineered with human Ig heavy and light chain YACs. *Nat. Genet.*, 7(1):13-21 (1994).

Grzesiak et al., The integrin-extracellular matrix axis in pancreatic cancer. *Pancreas*, 35(4):293-301 (2007).

Grzesiak et al., Divalent cations modulate alpha2beta1 integrin-mediated malignancy in a novel 3-dimensional in vitro model of pancreatic cancer. *Pancreas*, 39(6):904-12 (2010).

Grzesiak et al., Knockdown of the beta(1) integrin subunit reduces primary tumor growth and inhibits pancreatic cancer metastasis. *Int. J. Cancer*, 129(12):2905-15 (2011).

Guo et al., Integrin signaling during tumour progression. *Nat. Rev. Mol. Cell Biol.*, 5(10):816-26 (2004).

Haas et al., In vivo inhibition of angiogenesis by interleukin-13 gene therapy in a rat model of rheumatoid arthritis. *Arthritis Rheum.*, 56(8):2535-48 (2007).

Hall et al., Type I collagen receptor (alpha 2 beta 1) signaling promotes the growth of human prostate cancer cells within the bone. *Cancer Res.*, 66(17):8648-54 (2006).

Harland et al., Translation of mRNA injected into *Xenopus* oocytes is specifically inhibited by antisense RNA. *J. Cell Biol.*, 101(3):1094-9 (1985).

Hathout et al., in vivo magnetic resonance imaging of vascularization in islet transplantation. *Transpl. Int.*, 20(12)1059-65 (2007).

Hollinger et al., Engineered antibody fragments and the rise of single domains. *Nat. Biotechnol.*, 23(9):1126-36 (2005).

Holtkotter et al., Integrin alpha 2-deficient mice develop normally, are fertile, but display partially defective platelet interaction with collagen. *J. Biol. Chem.*, 277(13):10789-94 (2002).

Huck et al., beta1-integrin is dispensable for the induction of ErbB2 mammary tumors but plays a critical role in the metastatic phase of tumor progression. *Proc. Natl. Acad. Sci. U.S.A.*, 107(35):15559-64 (2010).

Hwang et al., Use of human germline genes in a CDR homology-based approach to antibody humanization. *Methods*, 36(1):35-42 (2005).

(56) References Cited

OTHER PUBLICATIONS

Ibaragi et al., Induction of MMP-13 expression in bone-metastasizing cancer cells by type I collagen through integrin alphalbetal and alpha2beta1-p38 MAPK signaling. *Anticancer Res.*, 31(4):1307-13 (2011).
Isner et al., Arterial gene therapy for restenosis. *Hum. Gene Ther.*, 7(8):989-1011 (1996).
Isner et al., Arterial gene therapy for therapeutic angiogenesis in patients with peripheral artery disease. *Circulation*, 91(11):2687-92 (1995).
Jakobovits et al., Production of antigen-specific human antibodies from mice engineered with human heavy and light chain YACs. *Ann. N.Y. Acad. Sci.*, 764:525-35 (1995).
Jokinen et al., Integrin-mediated cell adhesion to type I collagen fibrils. *J. Biol. Chem.*, 279(30):31956-63 (2004).
Kaneda et al., Increased expression of DNA cointroduced with nuclear protein in adult rat liver. *Science*, 243(4889):375-8 (1989).
Kato et al., Expression of hepatitis B virus surface antigen in adult rat liver. Co-introduction of DNA and nuclear protein by a simplified liposome method. *J. Biol. Chem.*, 266(6):3361-4 (1991).
Kawashima et al., Tumour necrosis factor-alpha provokes upregulation of alpha2beta1 and alpha5beta1 integrins, and cell migration in OST osteosarcoma cells. *Cell Biol. Int.*, 25(4):319-29 (2001).
Kidera et al., Reduction of lung metastasis, cell invasion, and adhesion in mouse melanoma by statin-induced blockade of the Rho/Rho-associated coiled-coil-containing protein kinase pathway. *J. Exp. Clin. Cancer Res.*, 29:127 (2010).
Kim et al., Minimal requirement for a lentivirus vector based on human immunodeficiency virus type 1. *J. Virol.*, 72(1):811-6 (1998).
Kirkland et al., Alpha2beta1 integrin regulates lineage commitment in multipotent human colorectal cancer cells. *J. Biol. Chem.*, 283(41):27612-9 (2008).
Kirkland, Type I collagen inhibits differentiation and promotes a stem cell-like phenotype in human colorectal carcinoma cells. *Br. J. Cancer*, 101(2):320-6 (2009).
Klein et al., High velocity microprojectiles for delivering nucleic acids into living cells. *Nature*, 327:70-3 (1987).
Klein et al., Identification of a melanoma progression antigen as integrin VLA-2. *J. Invest. Dermatol.*, 96(2):281-4 (1991).
Korhonen et al., Endothelial-specific gene expression directed by the tie gene promoter in vivo. *Blood*, 86(5):1828-35 (1995).
Lang et al., Primary prostatic epithelial cell binding to human bone marrow stroma and the role of alpha2beta1 integrin. *Clin. Exp. Metastasis*, 15(3):218-27 (1997).
Langsenlehner et al., Integrin alpha-2 and beta-3 gene polymorphisms and breast cancer risk. *Breast Cancer Res. Treat.*, 97(1):67-72 (2006).
Lee et al., alpha2 Integrin-Dependent Suppression of Pancreatic Adenocarcinoma Cell Invasion Involves Ectodomain Regulation of Kallikrein-Related Peptidase-5. *J. Oncol.*, 2011:365651 (2011).
Lee et al., Biomarkers for assessment of pharmacologic activity for a vascular endothelial growth factor (VEGF) receptor inhibitor, PTK787/ZK 222584 (PTK/ZK): translation of biological activity in a mouse melanoma metastasis model to phase I studies in patients with advanced colorectal cancer with liver metastases. *Cancer Chemother. Pharmacol.*, 57(6):761-71 (2006).
Lehner et al., Comparative sequence analysis of human cytomegalovirus strains. *J. Clin. Microbiol.*, 29(11):2494-502 (1991).
Liu et al., Cyclooxygenase-2 enhances alpha2beta1 integrin expression and cell migration via EP1 dependent signaling pathway in human chondrosarcoma cells. *Mol. Cancer*, 9:43 (2010).
Lonberg et al., Antigen-specific human antibodies from mice comprising four distinct genetic modifications. *Nature*, 368(6474):856-9 (1994).
Matsuoka et al., Increased expression of alpha2beta1-integrin in the peritoneal dissemination of human gastric carcinoma. *Int. J. Mol. Med.*, 5(1):21-5 (2000).

Miles et al., In vivo assessment of neovascularization of liver metastases using perfusion CT. *Br. J. Radiol.*, 71 (843):276-81 (1998).
Miller et al., Small-molecule inhibitors of integrin alpha2beta1 that prevent pathological thrombus formation via an allosteric mechanism. *Proc. Natl. Acad. Sci. U.S.A.*, 106(3):719-24 (2009).
Mita et al., Phase I study of E7820, an oral inhibitor of integrin alpha-2 expression with antiangiogenic properties, in patients with advanced malignancies. *Clin. Cancer Res.*, 17(1):193-200 (2011).
Miyake et al., Transforming growth factor-beta1 stimulates contraction of human glioblastoma cell-mediated collagen lattice through enhanced alpha2 integrin expression. *J. Neuropathol. Exp. Neurol.*, 59(1):18-28 (2000).
Mohammed et al., Effects of the cyclooxygenase inhibitor, piroxicam, in combination with chemotherapy on tumor response, apoptosis, and angiogenesis in a canine model of human invasive urinary bladder cancer. *Mol. Cancer Ther.*, 2(2):183-8 (2003).
Nicolau et al., Liposome-mediated DNA transfer in eukaryotic cells. Dependence of the transfer efficiency upon the type of liposomes used and the host cell cycle stage. *Biochim Biophys. Acta*, 721(2):185-90 (1982).
Nisonoff et al., Separation of univalent fragments from the bivalent rabbit antibody molecule by reduction of disulfide bonds. *Arch. Biochem. Biophys.*, 89:230-44 (1960).
Nissinen et al., Transcription of alpha2 integrin gene in osteosarcoma cells is enhanced by tumor promoters. *Exp. Cell Res.*, 243(1):1-10 (1998).
Ota et al., Induction of a MT1-MMP and MT2-MMP-dependent basement membrane transmigration program in cancer cells by Snail1. *Proc. Natl. Acad. Sci. U.S.A.*, 106(48):20318-23 (2009).
Paulus et al., Characterization of integrin receptors in normal and neoplastic human brain. *Am. J. Pathol.*, 143(1):154-63 (1993).
Pluckthun et al., Expression of functional antibody Fv and Fab fragments in *Escherichia coli*. *Methods Enzymol.*, 178:497-515 (1989).
Porter, The hydrolysis of rabbit y-globulin and antibodies with crystalline papain. *Biochem. J.*, 73:119-26 (1959).
Potter et al., Enhancer-dependent expression of human kappa immunoglobulin genes introduced into mouse pre-B lymphocytes by electroporation. *Proc. Natl. Acad. Sci. U.S.A.*, 81(22):7161-5 (1984).
Quantin et al., Adenovirus as an expression vector in muscle cells in vivo. *Proc. Natl. Acad. Sci. U.S.A.*, 89(7):2581-4 (1992).
Radler et al., Structure of DNA-cationic liposome complexes: DNA intercalation in multilamellar membranes in distinct interhelical packing regimes. *Science*, 275(5301):810-4 (1997).
Ramaswamy et al., A molecular signature of metastasis in primary solid tumors. *Nat. Genet.*, 33(1):49-54 (2003).
Ramirez et al., The alpha2beta1 integrin is a metastasis suppressor in mouse models and human cancer. *J. Clin. Invest.*, 121(1):226-37 (2011).
Rippe et al., DNA-mediated gene transfer into adult rat hepatocytes in primary culture. *Mol. Cell Biol.*, 10(2):689-95 (1990).
Rosenfeld et al., In vivo transfer of the human cystic fibrosis transmembrane conductance regulator gene to the airway epithelium. *Cell*, 68(1):143-55 (1992).
San Antonio, A key role for the integrin alpha2beta1 in experimental and developmental angiogenesis. *Am. J. Pathol.*, 175(3):1338-47 (2009).
Sawada et al., Integrin inhibitors as a therapeutic agent for ovarian cancer. *J. Oncol.*, 2012:915140 (2012).
Schneider et al., Integrins and bone metastasis: integrating tumor cell and stromal cell interactions. *Bone*, 48(1):54-65 (2011).
Semba et al., An angiogenesis inhibitor E7820 shows broad-spectrum tumor growth inhibition in a xenograft model: possible value of integrin alpha2 on platelets as a biological marker. *Clin. Cancer Res.*, 10(4):1430-8 (2004).
Senger et al., The alpha(1)beta(1) and alpha(2)beta(1) integrins provide critical support for vascular endothelial growth factor signaling, endothelial cell migration, and tumor angiogenesis. *Am. J. Pathol.*, 160(1):195-204 (2002).
Shield et al., Alpha2beta1 integrin affects metastatic potential of ovarian carcinoma spheroids by supporting disaggregation and proteolysis. *J. Carcinog.*, 6:11 (2007).

(56) References Cited

OTHER PUBLICATIONS

Shroyer et al., Intestine-specific ablation of mouse atonal homolog 1 (Math1) reveals a role in cellular homeostasis. Gastroenterology, 132(7):2478-88 (2007).

Skubitz et al., Expression of alpha 6 and beta 4 integrins in serous ovarian carcinoma correlates with expression of the basement membrane protein laminin. *Am. J. Pathol.*, 148(5):1445-61 (1996).

Soikkeli et al., Metastatic outgrowth encompasses COL-I, FN1, and POSTN up-regulation and assembly to fibrillar networks regulating cell adhesion, migration, and growth. Am. J. Pathol., 177(1):387-403 (2010).

Stratford-Perricaudet et al., Widespread long-term gene transfer to mouse skeletal muscles and heart. *J. Clin. Invest.*, 90(2):626-30 (1992).

Tabatabai et al., Targeting integrins in malignant glioma. *Target Oncol.*, 5(3):175-81 (2010).

Tamura et al., Structural correlates of an anticarcinoma antibody: identification of specificity-determining residues (SDRs) and development of a minimally immunogenic antibody variant by retention of SDRs only. *J. Immunol.*, 164(3):1432-41 (2000).

Taylor et al., Human immunoglobulin transgenes undergo rearrangement, somatic mutation and class switching in mice that lack endogenous IgM. *Int. Immunol.*, 6(4):579-91 (1994).

Taylor, VEGF and imaging of vessels in rheumatoid arthritis. *Arthritis Res.*, 4 Suppl. 3:S99-107 (2002).

Trerotola et al., CD133, Trop-2 and alpha2beta1 integrin surface receptors as markers of putative human prostate cancer stem cells. *Am. J. Transl. Res.*, 2(2):135-44 (2010).

Tucker, Integrins: molecular targets in cancer therapy. *Curr. Oncol. Rep.*, 8(2):96-103 (2006).

Tur-Kaspa et al., Use of electroporation to introduce biologically active foreign genes into primary rat hepatocytes. *Mol. Cell Biol.*, 6(2):716-8 (1986).

Van Kempen et al., Type I collagen expression contributes to angiogenesis and the development of deeply invasive cutaneous melanoma. *Int. J. Cancer*, 122(5):1019-29 (2008).

Van Slambrouk et al., Reorganization of the integrin alpha2 subunit controls cell adhesion and cancer cell invasion in prostate cancer. *Int. J. Oncol.*, 34(6):1717-26 (2009).

Vuoristo et al., Increased gene expression levels of collagen receptor integrins are associated with decreased survival parameters in patients with advanced melanoma. *Melanoma Res.*, 17(4):215-23 (2007).

Weinel et al., Expression and function of VLA-alpha 2, -alpha 3, -alpha 5 and -alpha 6- integrin receptors in pancreatic carcinoma. Int. J. Cancer, 52(5):827-33 (1992).

Wu et al., Evidence for targeted gene delivery to Hep G2 hepatoma cells in vitro. Biochemistry, 27(3):887-92 (1988).

Wu et al., Liver-directed gene delivery. Adv. Drug Delivery Rev., 12(3):159-67 (1993).

Wu et al., Receptor-mediated in vitro gene transformation by a soluble DNA carrier system. J. Biol. Chem., 262(10):4429-32 (1987).

Yang et al., In vivo and in vitro gene transfer to mammalian somatic cells by particle bombardment. *Proc. Natl. Acad. Sci. U.S.A.*, 87(24):9568-72 (1990).

Yang et al., Integrin alpha1beta1 and alpha2beta1 are the key regulators of hepatocarcinoma cell invasion across the fibrotic matrix microenvironment. *Cancer Res.*, 63(23):8312-7 (2003).

Yao et al., Increased beta1 integrin is associated with decreased survival in invasive breast cancer. *Cancer Res.*, 67(2):659-64 (2007).

Yoshimura et al., Integrin alpha2 mediates selective metastasis to the liver. *Cancer Res.*, 69(18):7320-8 (2009).

Zhang et al., Humanization of an anti-human TNF-alpha antibody by variable region resurfacing with the aid of molecular modeling. *Mol. Immunol.*, 42(12):1445-51 (2005).

\* cited by examiner

INTEGRIN ALPHA-2 BINDING AGENTS AND USE THEREOF TO INHIBIT CANCER CELL PROLIFERATION

CROSS REFERENCE TO RELATED APPLICATIONS

This application claims priority to U.S. Provisional Application No. 61/487,812, filed May 19, 2011, which is hereby incorporated by reference in its entirety.

INCORPORATION BY REFERENCE OF MATERIAL SUBMITTED ELECTRONICALLY

Incorporated by reference in its entirety is a computer-readable sequence listing submitted concurrently herewith and identified as follows: ASCII (Text) file named "46156A_SeqListing," 223,158 bytes, created on May 14, 2012.

FIELD OF THE INVENTION

The disclosure generally relates to integrin alpha-2 binding agents, uses thereof, and methods of screening for therapeutically effective antibodies.

BACKGROUND OF THE INVENTION

Integrins are a family of α/β heterodimeric transmembrane receptors found throughout metazoan development. Integrins are involved in various aspects of cellular behavior. For example, they mediate attachment to extracellular matrix (ECM) proteins and link the extracellular environment with intracellular signaling events. Integrin-mediated cell adhesions induce cell signaling that triggers calcium fluxes, activates tyrosine and serine/threonine protein kinases and inositol lipid metabolism, and regulates the activity of GTPases that control the actin cytoskeleton. Besides mediating stable adhesion, integrins play a role in cellular motility. Cell migration is essential for embryonic development, immune responses, and tissue repair.

In humans, there are 24 different functional integrins formed by the different combination of 18 alpha (α) and 8 beta (β) subunits. Many integrins bind to components of the extracellular matrix (ECM) such as laminins, collagens, and fibronectin. The integrin alpha-2 beta-1 (α2β1), for example, binds Type I collagen, the dominant ECM protein in the body. Integrin alpha-2 is one of the twelve α integrins that forms a functional receptor with the integrin beta 1 ($β_1$) subunit. Integrin alpha-2 has only been found in vertebrates, and in humans, it is widely expressed on mesenchymal, epithelial and endothelial cells. Platelets also use integrin alpha-2 as their collagen receptor. Integrin alpha-2 has been implicated in hepatocarcinoma cell invasion across the fibrotic matrix microenvironment (Yang et al., *Cancer Res.*, 63, 8312 (2003)), in metastasis of ovarian carcinoma spheroids (Shield et al., *J. Carcinogenesis*, 6, 11 (2007)), in metastasis to the liver (Yoshimura et al., *Cancer Res.*, 69:18, 7320 (2009)), and in adhesion and cancer cell invasion in prostate cancer (Van Slambrouk et al., *Int. J. Oncology*, 34, 1717 (2009)).

Cancer remains a leading cause of death worldwide, with an estimated 500,000 Americans succumbing to the disease in 2010 (American Cancer Society. Cancer Facts & Figures 2010. Atlanta, American Cancer Society; 2010). There remains a need in the art for therapeutics, and methods of using such therapeutics, that are effective in treating, preventing, or ameliorating cancer cell proliferation.

SUMMARY OF THE INVENTION

The invention provides an integrin alpha-2 binding agent that cross-blocks the binding of at least one of antibodies 770.8, 778.17, and 774.3 to integrin alpha-2 and/or is cross-blocked from binding to integrin alpha-2 by at least one of antibodies 770.8, 778.17, and 774.3.

The invention further provides an integrin alpha-2 binding agent that comprises at least one CDR sequence having at least 75% identity to a CDR selected from SEQ ID NOs: 1, 2, 3, 4, 5, 6, 7, 8, 9, 11, 12, 13, 14, 15, 16, 17, and 18. For example, in one aspect, the integrin alpha-2 binding agent comprises: (a) a heavy chain comprising a polypeptide having the sequence provided in SEQ ID NO: 19, and a light chain comprising a polypeptide having the sequence provided in SEQ ID NO: 20; (b) a heavy chain comprising a polypeptide having the sequence provided in SEQ ID NO: 21, and a light chain comprising a polypeptide having the sequence provided in SEQ ID NO: 22; or (c) a heavy chain comprising a polypeptide having the sequence provided in SEQ ID NO: 23, and a light chain comprising a polypeptide having the sequence provided in SEQ ID NO: 24. In various aspects, the integrin alpha-2 binding agent is an antibody, e.g., an immunoglobulin having heavy and light chains. In various aspects, the integrin alpha-2 binding agent is an antibody fragment. An isolated polynucleotide encoding the integrin alpha-2 binding agent, a process for producing the integrin alpha-2 binding agent, and a pharmaceutical composition comprising the integrin alpha-2 binding agent also are provided.

The invention also provides an integrin alpha-2 binding agent that binds one or both of SEQ ID NO: 32 and SEQ ID NO: 33. In one aspect, the integrin alpha-2 binding agent binds SEQ ID NO: 32 and SEQ ID NO: 33. In various aspects, the integrin alpha-2 binding agent inhibits proliferation of cancer cells in three-dimensional cell culture. In various aspects, the integrin alpha-2 binding agent is an antibody, e.g., an immunoglobulin having heavy and light chains, or a fragment thereof.

Additionally, the invention includes a method of inhibiting proliferation of cancer cells. The method comprises contacting cancer cells with an amount of an integrin alpha-2 binding agent effective to inhibit proliferation of the cancer cells. In various embodiments, the cancer cells are in a subject, and the contacting comprises administering the integrin alpha-2 binding agent to the subject. The invention further includes a method of modulating tumor growth in a subject, the method comprising administering to the subject a composition comprising an integrin alpha-2 binding agent in an amount effective to modulate tumor growth in the subject.

Methods of producing an antibody and screening agents for cancer cell inhibitory activity also are provided. For example, the invention includes a method of producing an antibody comprising the steps of (a) propagating cancer cells in a 3-dimensional matrix; (b) immunizing a mammal with the propagated cancer cells; and (c) isolating an antibody or antigen-binding fragment thereof from the immunized mammal. Optionally, the method further comprises (d) testing the antibody or antigen-binding fragment thereof for anti-cancer activity. Also included in the invention is a method of identifying an agent that inhibits cancer cell proliferation, the method comprising the steps of (a) performing a competition assay with a candidate agent and an antibody selected from the group consisting of antibody 770.8, antibody 778.17, and antibody 774.3 or an antigen-binding fragment of any of the foregoing. The method further comprises isolating a candidate agent that (i) is blocked from binding an integrin alpha-2 polypeptide of SEQ ID NO: 25 by antibody 770.8, antibody 778.17, antibody 774.3, or an antigen-binding fragment of any of the foregoing or (ii) blocks binding of antibody 770.8, antibody 778.17, antibody 774.3, or an antigen-binding fragment of any of the foregoing to integrin alpha-2.

Methods of treating fibrotic disorders are also provided. For example, the invention includes a method of treating a fibrotic disorder in a subject comprising administering to the subject a composition comprising an integrin alpha-2 binding agent, such as one of antibodies 770.8, 778.17, and 774.3. In some aspects, the fibrotic disorder is selected from the group consisting of chronic kidney disease, chronic liver disease, lung fibrosis, systemic sclerosis, organ transplant fibrosis, endomyocardial fibrosis, mediastinal fibrosis, myelofibrosis, retroperitoneal fibrosis, progressive massive fibrosis, nephrogenic systemic fibrosis, Crohn's Disease, and arthrofibrosis.

Methods of inhibiting angiogenesis are also provided. For example, the invention includes a method of inhibiting angiogenesis in a subject comprising administering to the subject a composition comprising an integrin alpha-2 binding agent, such as one of antibodies 770.8, 778.17, and 774.3, in an amount effective to inhibit angiogenesis in the subject.

Other features and advantages of the present disclosure will become apparent from the following detailed description. It should be understood, however, that the detailed description and the specific examples, while indicating specific embodiments of the disclosure, are given by way of illustration only, because various changes and modifications within the spirit and scope of the disclosure will become apparent to those skilled in the art from this detailed description. The entire document is intended to be related as a unified disclosure, and it should be understood that all combinations of features described herein are contemplated, even if the combination of features are not found together in the same sentence, or paragraph, or section of this document. In addition to the foregoing, the invention includes, as an additional aspect, all embodiments of the invention narrower in scope in any way than the variations specifically mentioned above. For example, if aspects of the invention are described as "comprising" a feature, embodiments also are contemplated "consisting of" or "consisting essentially of" the feature.

DETAILED DESCRIPTION OF THE INVENTION

The invention provides integrin alpha-2 binding agents (e.g., antibodies or antibody fragments) and methods of using integrin alpha-2 binding agents to, e.g., inhibit proliferation of cancer cells. An exemplary amino acid sequence of integrin alpha-2 is provided as SEQ ID NO: 25. The α2β1 heterodimer is a high-affinity receptor for many collagen subtypes. An inserted domain, i.e., the I domain (also called an A domain), in integrin alpha-2 facilitates recognition of collagenous ligands. Integrin alpha-2 shares these features (the presence of alpha I domain and functional features of collagen binding and partnering with (β1) with integrin alpha-1, integrin alpha-10 and integrin alpha-11. In addition to collagens, integrin α2β1 binds to several other proteins, including laminins, endorepellin and decorin.

The invention includes an integrin alpha-2 binding agent that cross-blocks the binding of at least one of antibodies 770.8, 778.17, and 774.3 to integrin alpha-2 and/or is cross-blocked from binding to integrin alpha-2 by at least one of antibodies 770.8, 778.17, and 774.3. An "integrin alpha-2 binding agent" specifically binds to integrin alpha-2 or portions thereof to block or impair binding of antibodies 770.8, 778.17, or 774.3 human integrin alpha-2 and, optionally, to block or impair binding of human integrin alpha-2 to one or more ligands, such as the ligands described herein. In this regard, the integrin alpha-2 binding agent preferably binds integrin alpha-2 expressed on the surface of a mammalian (e.g., human) cell. In various embodiments, the integrin alpha-2 binding agent binds an integrin alpha-2 extracellular epitope exposed on a cancer cell. Optionally, the integrin alpha-2 comprises the amino acid sequence set forth in SEQ ID NO: 25. The invention also provides an integrin alpha-2 binding agent that binds an epitope of integrin alpha-2 that is bound by Ab 770.8, Ab 778.17, or Ab 774.3.

In various embodiments, the integrin alpha-2 binding agent is an antibody, antibody fragment, or other peptide-based molecule. Any type of antibody is suitable in the context of the invention, including polyclonal, monoclonal, chimeric, humanized, or human versions having full length heavy and/or light chains. The invention also includes antibody fragments (and/or polypeptides that comprise antibody fragments) that retain integrin alpha-2 binding characteristics. Antibody fragments include antigen-binding regions and/or effector regions of the antibody, e.g., F(ab')2, Fab, Fab', Fd, Fc, and Fv fragments (fragments consisting of the variable regions of the heavy and light chains that are non-covalently coupled), or single-domain antibodies (nanobodies). In general terms, a variable (V) region domain may be any suitable arrangement of immunoglobulin heavy ($V_H$) and/or light ($V_L$) chain variable domains. Thus, for example, the V region domain may be dimeric and contain $V_H$-$V_H$, $V_H$-$V_L$, or $V_L$-$V_L$ dimers that bind integrin alpha-2. If desired, the $V_H$ and $V_L$ chains may be covalently coupled either directly or through a linker to form a single chain Fv (scFv). For ease of reference, scFv proteins are referred to herein as included in the category "antibody fragments." Another form of an antibody fragment is a peptide comprising one or more complementarity determining regions (CDRs) of an antibody. CDRs (also termed "minimal recognition units" or "hypervariable region") can be obtained by constructing polynucleotides that encode the CDR of interest. Such polynucleotides are prepared, for example, by using the polymerase chain reaction to synthesize the variable region using mRNA of antibody-producing cells as a template (see, for example, Larrick et al., *Methods: A Companion to Methods in Enzymology,* 2:106 (1991); Courtenay-Luck, "Genetic Manipulation of Monoclonal Antibodies," in *Monoclonal Antibodies Production, Engineering and Clinical Application*, Ritter et al. (eds.), page 166, Cambridge University Press (1995); and Ward et al., "Genetic Manipulation and Expression of Antibodies," in *Monoclonal Antibodies: Principles and Applications*, Birch et al., (eds.), page 137, Wiley-Liss, Inc. (1995)). Antibody fragments may be incorporated into single domain antibodies, maxibodies, minibodies, intrabodies, diabodies, triabodies, tetrabodies, variable domains of new antigen receptors (v-NAR), and bis-single chain Fv regions (see, e.g., Hollinger and Hudson, *Nature Biotechnology*, 23 (9): 1126-1136, 2005). The binding agent, in some embodiments, contains a light chain and/or a heavy chain constant region, such as the IgG4 or the IgG2 constant region.

If desired, the antibody or antibody fragment (or other integrin alpha-2 binding agent) is connected or fused to a moiety with effector function, such as cytotoxic activity (e.g., a chemotherapeutic moiety or a radioisotope) or immune recruitment activity. Alternatively or in addition, the antibody or antibody fragment (or other integrin alpha-2 binding agent) is optionally connected or fused to a moiety that facilitates isolation from a mixture (e.g., a tag) or a moiety with reporter activity (e.g., a detection label or reporter protein). It will be appreciated that the features of the inventive antibody or fragment thereof described herein extend also to a polypeptide comprising the antibody fragment.

The antibody or antibody fragment is produced using any suitable method, e.g., isolated from an immunized animal, recombinantly or synthetically generated, or genetically-engineered. Antibody fragments derived from an antibody are obtained by, e.g., proteolytic hydrolysis of an antibody. For example, papain or pepsin digestion of whole antibodies yields a 5S fragment termed F(ab')$_2$ or two monovalent Fab fragments and an Fc fragment, respectively. F(ab)$_2$ can be further cleaved using a thiol reducing agent to produce 3.5S Fab monovalent fragments. Methods of generating antibody fragments are further described in, for example, Edelman et al., Methods in Enzymology, 1: 422 Academic Press (1967); Nisonoff et al., Arch. Biochem. Biophys., 89: 230-244, 1960; Porter, Biochem. J., 73: 119-127, 1959; U.S. Pat. No. 4,331, 647; and by Andrews, S. M. and Titus, J. A. in Current Protocols in Immunology (Coligan et al., eds), John Wiley & Sons, New York (2003), pages 2.8.1 2.8.10 and 2.10A.1 2.10A.5.

An antibody or fragment thereof also can be genetically engineered. For example, in various aspects, the antibody or antibody fragment comprises, e.g., a variable region domain generated by recombinant DNA engineering techniques. In this regard, an antibody variable region is optionally modified by insertions, deletions, or changes in the amino acid sequence of the antibody to produce an antibody of interest. Polynucleotides encoding complementarity determining regions (CDRs) of interest are prepared, for example, by using polymerase chain reaction to synthesize variable regions using mRNA of antibody producing cells as a template (see, for example, Courtenay Luck, "Genetic Manipulation of Monoclonal Antibodies," in Monoclonal Antibodies: Production, Engineering and Clinical Application, Ritter et al. (eds.), page 166 (Cambridge University Press 1995); Ward et al., "Genetic Manipulation and Expression of Antibodies," in Monoclonal Antibodies: Principles and Applications, Birch et al., (eds.), page 137 (Wiley Liss, Inc. 1995); and Larrick et al., Methods: A Companion to Methods in Enzymology, 2: 106-110, 1991). Current antibody manipulation techniques allow construction of engineered variable region domains containing at least one CDR and, optionally, one or more framework amino acids from a first antibody and the remainder of the variable region domain from a second antibody. Such techniques are used, e.g., to humanize an antibody or to improve its affinity for a binding target.

"Humanized antibodies" are antibodies in which CDRs of heavy and light variable chains of non-human immunoglobulin are transferred into a human variable domain. Constant regions need not be present, but if they are, they optionally are substantially identical to human immunoglobulin constant regions, i.e., at least about 85-90%, about 95% or more identical, in various embodiments. Hence, in some instances, all parts of a humanized immunoglobulin, except possibly the CDRs, are substantially identical to corresponding parts of natural human immunoglobulin sequences. For example, in one aspect, humanized antibodies are human immunoglobulins (host antibody) in which hypervariable region residues of the host antibody are replaced by hypervariable region residues from a non-human species (donor antibody) such as mouse, rat, rabbit, or a non-human primate having the desired specificity, affinity, and capacity.

In one embodiment, the antibody is a human antibody, such as, but not limited to, an antibody having variable regions in which both the framework and CDR regions are derived from human germline immunoglobulin sequences as described, for example, in Kabat et al. (1991) Sequences of proteins of Immunological Interest, Fifth Edition, U.S. Department of Health and Human Services, NIH Publication No. 91-3242. If the antibody contains a constant region, the constant region also preferably is derived from human germline immunoglobulin sequences. Human antibodies may comprise amino acid residues not encoded by human germline immunoglobulin sequences to, e.g., enhance the activity of the antibody, but do not comprise CDRs derived from other species (i.e., a mouse CDR placed within a human variable framework region).

The antibody or fragment thereof preferably preferentially binds to integrin alpha-2, meaning that the antibody or fragment thereof binds integrin alpha-2 with greater affinity than it binds to an unrelated control protein. More preferably, the antibody or fragment thereof specifically recognizes and binds integrin alpha-2 (or a portion thereof). "Specific binding" means that the antibody or fragment thereof binds to integrin alpha-2 with an affinity that is at least 5, 10, 15, 20, 25, 50, 100, 250, 500, 1000, or 10,000 times greater than the affinity for an unrelated control protein (e.g., hen egg white lysozyme). In some variations of the invention, the antibody or fragment thereof binds integrin alpha-2 substantially exclusively (i.e., is able to distinguish integrin alpha-2 from other known polypeptides (e.g., other integrins) by virtue of measurable differences in binding affinity). In other variations, the integrin alpha-2 binding agent cross-reacts with other integrin sequences.

In at least one embodiment, integrin alpha-2 binding agent cross-blocks the binding of at least one of antibodies 770.8, 778.17, and 774.3 to integrin alpha-2. Alternatively or in addition, integrin alpha-2 binding agent is cross-blocked from binding to integrin alpha-2 by at least one of antibodies 770.8, 778.17, and 774.3. The terms "cross-block," "cross-blocked," and "cross-blocking" are used interchangeably herein to mean the ability of an antibody or other binding agent to interfere with the binding of other antibodies or binding agents to integrin alpha-2. The extent to which an antibody or other binding agent is able to interfere with the binding of another to integrin alpha-2, and therefore whether it can be said to cross-block, can be determined using competition binding assays. In some aspects of the invention, a cross-blocking antibody or fragment thereof reduces integrin alpha-2 binding of a reference antibody between about 40% and about 100%, such as about 60% and about 100%, specifically between 70% and 100%, and more specifically between 80% and 100%. A particularly suitable quantitative assay for detecting cross-blocking and/or determining binding specific/affinity of an antibody uses a Biacore machine which measures the extent of interactions using surface plasmon resonance technology. Another suitable quantitative cross-blocking assay uses an ELISA-based approach to measure competition between antibodies or other binding agents in terms of their binding to integrin alpha-2, which also is suitable for determining binding specific/affinity of an antibody.

Examples of suitable integrin alpha-2 binding agents include all or part of the antigen-binding elements of Ab 770.8, Ab 778.17, or Ab 774.3, including the variable region of Ab 770.8, Ab 778.17, or Ab 774.3 (or any other antibody of the invention). For example, integrin alpha-2 binding agent optionally comprises all or part of the antigen-binding elements of Ab 770.8, Ab 778.17, or Ab 774.3 while lacking all or part of the framework regions of the antibody. In this regard, the integrin alpha-2 binding agent optionally comprises one, two, three, four, five, or six (i.e., all) complementary determining regions (CDRs) of Ab 770.8, Ab 778.17, or Ab 774.3 (or another integrin alpha-2-binding antibody that inhibits cancer cell proliferation). Methods of identifying complementarity determining regions and specificity determining regions are known in the art and further described in, for example, Tamura et al., *J. Immunol.*, 164: 1432-1441, 2000.

In various embodiments, the antibody or fragment thereof comprises one or more of CDR-H1, CDR-H2, CDR-H3, CDR-L1, CDR-L2 and CDR-L3. At least one of the regions of CDR-H1, CDR-H2, CDR-H3, CDR-L1, CDR-L2 and CDR-L3 may have at least one amino acid substitution, provided that the binding agent retains the binding specificity of the non-substituted CDR. The non-CDR portion of the binding agent may be a non-protein molecule, wherein the binding agent cross-blocks the binding of an antibody disclosed herein to integrin alpha-2 and/or neutralizes integrin alpha-2. The non-CDR portion of the binding agent may be a non-protein molecule in which the binding agent exhibits a similar binding pattern to human integrin alpha-2 peptides in a "human integrin alpha-2 peptide epitope competition binding assay" as that exhibited by at least one of Ab 770.8, Ab 778.17, or Ab 774.3, and/or neutralizes integrin alpha-2. The non-CDR portion of the binding agent may be composed of amino acids, wherein the binding agent is a recombinant binding protein or a synthetic peptide, and the recombinant binding protein cross-blocks the binding of an antibody disclosed herein to integrin alpha-2 and/or neutralizes integrin alpha-2. The non-CDR portion of the binding agent may be composed of amino acids, wherein the binding agent is a recombinant binding protein, and the recombinant binding protein exhibits a similar binding pattern to human integrin alpha-2 peptides in a human integrin alpha-2 peptide epitope competition binding assay as that exhibited by at least one of the mAb 770.8, mAb 778.17, or mAb 774.3, and/or neutralizes integrin alpha-2.

Where an integrin alpha-2 binding agent comprises one or more of CDR-H1, CDR-H2, CDR-H3, CDR-L1, CDR-L2 and CDR-L3 as described above, it may be obtained by expression from a host cell containing DNA coding for these sequences. A DNA coding for each CDR sequence may be determined on the basis of the amino acid sequence of the CDR and synthesized together with any desired antibody variable region framework and constant region DNA sequences using oligonucleotide synthesis techniques, site directed mutagenesis and polymerase chain reaction (PCR) techniques as appropriate. DNA coding for variable region frameworks and constant regions is widely available to those skilled in the art from genetic sequences databases such as GenBank®. CDRs typically are located in a variable region framework at positions 31-35 (CDR-H1), 50-65 (CDR-H2) and 95-102 (CDR-H3) of the heavy chain and positions 24-34 (CDR-L1), 50-56 (CDR-L2) and 89-97 (CDR-L3) of the light chain according to the Kabat numbering system (Kabat et al., 1987 in Sequences of Proteins of Immunological Interest, U.S. Department of Health and Human Services, NIH, USA).

In various embodiments, the integrin alpha-2 binding agent comprises at least one CDR sequence having at least 75% identity (e.g., at least 85% identity or 100% identity) to a CDR selected from SEQ ID NOs: 1-18. Preferably, the integrin alpha-2 binding agent comprises CDR sequences having at least 75% identity (e.g., at least 85% identity or 100% identity) to at least two of the CDRs, at least three of the CDRs, at least four of the CDRs, at least five of the CDRs, or at least six of the CDRs. For example, suitable integrin alpha-2 binding agents include, but are not limited to, binding agents comprising a) CDR sequences of SEQ ID NOs: 1, 2, and 3; b) CDR sequences of SEQ ID NOs: 4, 5, and 6; c) CDR sequences of SEQ ID NOs: 7, 8, and 9; d) CDR sequences of SEQ ID NOs: 10, 11, and 12; e) CDR sequences of SEQ ID NOs: 13, 14, and 15; or f) CDR sequences of SEQ ID NOs: 16, 17, and 18, such as integrin alpha-2 binding agents comprising CDR sequences of SEQ ID NOs: 1, 2, 3, 4, 5, and 6; CDR sequences of SEQ ID NOs: 7, 8, 9, 10, 11, and 12; or CDR sequences of SEQ ID NOs: 13, 14, 15, 16, 17, and 18.

In one aspect, the integrin alpha-2 binding agent comprises at least one CDR sequence having at least 75% identity to a CDR selected from CDR-H1, CDR-H2, CDR-H3, CDR-L1, CDR-L2 and CDR-L3 wherein CDR-H1 has the sequence given in SEQ ID NO: 1, SEQ ID NO: 7 or SEQ ID NO: 13, CDR-H2 has the sequence given in SEQ ID NO: 2, SEQ ID NO: 8 or SEQ ID NO: 14, CDR-H3 has the sequence given in SEQ ID NO: 3, SEQ ID NO: 9 or SEQ ID NO: 15, CDR-L1 has the sequence given in SEQ ID NO: 4, SEQ ID NO: 10 or SEQ ID NO: 16, CDR-L2 has the sequence given in SEQ ID NO: 5, SEQ ID NO: 11 or SEQ ID NO: 17 and CDR-L3 has the sequence given in SEQ ID NO: 6, SEQ ID NO: 12 or SEQ ID NO: 18. Optionally, the integrin alpha-2 binding agent comprises three CDRs, CDR-H1, CDR-H2 and CDR-H3 wherein (a) CDR-H1 is SEQ ID NO: 1, CDR-H2 is SEQ ID NO: 2, and CDR-H3 is SEQ ID NO: 3, (b) CDR-H1 is SEQ ID NO: 7, CDR-H2 is SEQ ID NO: 8, and CDR-H3 is SEQ ID NO: 9, or (c) CDR-H1 is SEQ ID NO: 13, CDR-H2 is SEQ ID NO: 14, and CDR-H3 is SEQ ID NO: 15. Alternatively or in addition, the integrin alpha-2 binding agent comprises three CDRs, CDR-L1, CDR-L2 and CDR-L3 wherein (a) CDR-L1 is SEQ ID NO: 4, CDR-L2 is SEQ ID NO: 5, and CDR-L3 is SEQ ID NO: 6, (b) CDR-L1 is SEQ ID NO: 10, CDR-L2 is SEQ ID NO: 11, and CDR-L3 is SEQ ID NO: 12, or (c) CDR-L1 is SEQ ID NO: 16, CDR-L2 is SEQ ID NO: 17, and CDR-L3 is SEQ ID NO: 18. In exemplary integrin alpha-2 binding agents (a) CDR-H1 is SEQ ID NO: 1, CDR-H2 is SEQ ID NO: 2, CDR-H3 is SEQ ID NO: 3, CDR-L1 is SEQ ID NO: 4, CDR-L2 is SEQ ID NO: 5 and CDR-L3 is SEQ ID NO: 6; CDR-H1 is SEQ ID NO: 7, CDR-H2 is SEQ ID NO: 8, CDR-H3 is SEQ ID NO: 9, CDR-L1 is SEQ ID NO: 10, CDR-L2 is SEQ ID NO: 11 and CDR-L3 is SEQ ID NO: 12; or CDR-H1 is SEQ ID NO: 13, CDR-H2 is SEQ ID NO: 14, CDR-H3 is SEQ ID NO: 15, CDR-L1 is SEQ ID NO: 16, CDR-L2 is SEQ ID NO: 17 and CDR-L3 is SEQ ID NO: 18.

Optionally, the integrin alpha-2 binding agent comprises a heavy chain comprising a polypeptide having at least 85% identity to the sequence given in SEQ ID NO: 19, SEQ ID NO: 21, or SEQ ID NO: 23 and/or a light chain comprising a polypeptide having at least 85% identity to the sequence given in SEQ ID NO: 20, SEQ ID NO: 22, or SEQ ID NO: 24. In this regard, the integrin alpha-2 binding agent, in various embodiments, comprising both a heavy chain and a light chain wherein (a) the heavy chain comprises a polypeptide having at least 85% identity to the sequence given in SEQ ID NO: 19 and the light chain comprises a polypeptide having at least 85% identity to the sequence given in SEQ ID NO: 20; (b) the heavy chain comprises a polypeptide having at least 85% identity to the sequence given in SEQ ID NO: 21 and the light chain comprises a polypeptide having at least 85% identity to the sequence given in SEQ ID NO: 22; or (c) the heavy chain comprises a polypeptide having at least 85% identity to the sequence given in SEQ ID NO: 23 and the light chain comprises a polypeptide having at least 85% identity to the sequence given in SEQ ID NO: 24. The integrin alpha-2 binding agent, in various aspects, comprises heavy chains comprising a polypeptide having the sequence provided in SEQ ID NO: 19, and light chains comprising a polypeptide having the sequence provided in SEQ ID NO: 20; heavy chains comprising a polypeptide having the sequence provided in SEQ ID NO: 21, and light chains comprising a polypeptide having the sequence provided in SEQ ID NO: 22; or heavy chains comprising a polypeptide having the sequence provided in SEQ ID NO: 23, and a light chain comprising a polypeptide having the sequence provided in SEQ ID NO: 24.

In one embodiment, the integrin alpha-2 binding agent is Ab 770.8 or an integrin alpha-2-binding fragment thereof. Ab 770.8 is a mouse antibody that binds human integrin alpha-2 and inhibits cancer cell proliferation. The amino acid sequence of the mature form (signal peptide removed) of Ab 770.8 light chain is shown in SEQ ID NO: 20: DIVMTQS-PAILSVSPGERVSFSCRASQSIGTSIHWYQQRTN-GSPRLLIKYVSESISGIPSR FSGSGSGTDFTLTINS-VESEDIADYYCQHSNRWPLTFGAGT-KLELKRADAAPTVS (SEQ ID NO: 20). The amino acid sequence of CDR-L1 is QSIGTS (SEQ ID NO: 4). The amino acid sequence of CDR-L2 is YVS (SEQ ID NO: 5). The amino acid sequence of CDR-L3 is QHSNRWPLT (SEQ ID NO: 6).

The nucleic acid sequence encoding the mature form (signal peptide removed) of Ab 770.8 light chain is SEQ ID NO: 27:

(SEQ ID NO: 27)
GATATTGTGATGACACAATCTCCAGCCATCCTGTCTGTGAGTCCAGGAG

AAAGAGTCAGTTTCTCCTGCAGGGCCAGTCAGAGCATTGGCACAAGCAT

ACACTGGTATCAGCAAAGAACAAATGGTTCTCCAAGGCTTCTCATAAAG

TATGTTTCTGAGTCTATCTCTGGGATCCCTTCCAGGTTTAGTGGCAGTG

GATCAGGGACAGATTTTACTCTTACCATCAACAGTGTGGAGTCTGAAGA

TATTGCAGATTATTACTGTCAACACAGTAATAGGTGGCCGCTCACGTTC

GGTGCTGGGACCAAGCTGGAGCTGAAACGGGCTGATGCTGCACCAACTG

TATCC.

The amino acid sequence of the mature form (signal peptide removed) of Ab 770.8 heavy chain is shown in SEQ ID NO: 19: EVKLEESGTVLARPGASVKMSCKASGYS-FTSYWMHWVKQRPGQGLEWIGAFYPGN SED-KYNENFKIKAKLTAVTSVNTVYMELSS-LTSEDSAVYYCTRGTTLVAPGFDVWG AGTTVTVSSAKTTPPSVYPLVP (SEQ ID NO: 19). The amino acid sequence of CDR-H1 is GYSFTSYW (SEQ ID NO: 1). The amino acid sequence of CDR-H2 is FYPGNSED (SEQ ID NO: 2). The amino acid sequence of CDR-H3 is TRGTTLVAPGFDV (SEQ ID NO: 3).

The nucleic acid sequence encoding the mature form (signal peptide removed) of Ab 770.8 heavy chain is SEQ ID NO: 26:

(SEQ ID NO: 26)
GAAGTGAAGCTGGAGGAGTCAGGGACTGTGCTGGCAAGGCCTGGGGCT

TCCGTGAAGATGTCCTGCAAGGCTTCTGGCTACAGTTTTACTAGCTAT

TGGATGCACTGGGTAAAACAGAGGCCTGGACAGGGTCTAGAATGGATT

GGTGCTTTTTATCCTGGAAATAGTGAAGATAAATATAACGAGAATTTC

AAGATCAAGGCCAAACTGACTGCAGTCACATCCGTCAATACTGTCTAC

ATGGAGCTCAGCAGCCTGACAAGTGAGGACTCTGCGGTCTATTATTGT

ACAAGAGGGACTACGTTAGTAGCTCCGGGCTTCGATGTCTGGGGCGCA

GGGACTACGGTCACCGTCTCCTCAGCCAAAACGACACCCCCATCTGTC

-continued
TATCCCTTGGTCCCT.

In one embodiment, the integrin alpha-2 binding agent is Ab 778.17 or an integrin alpha-2-binding fragment thereof. Ab 778.17 is a mouse antibody that binds integrin alpha-2 and inhibits cancer cell proliferation. The amino acid sequence of the mature form (signal peptide removed) of Ab 778.17 light chain is shown in SEQ ID NO: 22: DIVMTQTPTSLAVS-LGQRATISCRASESVDSYDNSFMYWYQQKPG-QPPKLLIYFASN LESGVPARFSGSGSRTDFTLTID-PVEADDAATYYCQQNNEDPYTFGGGTKLEIKRAD AAPTVS (SEQ ID NO: 22). The amino acid sequence of CDR-L1 is ESVDSYDNSF (SEQ ID NO: 10). The amino acid sequence of CDR-L2 is FAS (SEQ ID NO: 11). The amino acid sequence of CDR-L3 is QQNNEDPYT (SEQ ID NO: 12).

The nucleic acid sequence encoding the mature form (signal peptide removed) of Ab 778.17 light chain is SEQ ID NO: 29:

(SEQ ID NO: 29)
GATATTGTGATGACCCAGACTCCAACTTCTTTGGCTGTGTCTCTAGGG

CAGAGGGCCACCATATCCTGCAGAGCCAGTGAAAGTGTTGATAGTTAT

GACAACAGTTTTATGTATTGGTACCAGCAGAAACCAGGACAGCCACCC

AAACTCCTCATCTATTTTGCATCCAACCTAGAATCTGGGGTCCCTGCC

AGGTTCAGTGGCAGTGGGTCTAGGACAGACTTCACCCTCACCATTGAT

CCTGTGGAGGCTGATGATGCTGCAACCTATTACTGTCAGCAAAATAAT

GAGGATCCGTACACGTTCGGAGGGGGGACCAAGCTGGAAATAAAACGG

GCTGATGCTGCACCAACTGTATCC.

The amino acid sequence of the mature form (signal peptide removed) of Ab 778.17 heavy chain is shown in SEQ ID NO: 21: QVQLQQPGAELVRPGTSVKLSCKASGYT-FASYWMNWVSQRPEQGLEWIGRIDPYDS ETHYN-QKFKDKAILTVDKSSSTAYIQLNSLT-SEDSAVYYCARLGRGPFAYWGQGTLV TVSAAKTTPPSVY (SEQ ID NO: 21). The amino acid sequence of CDR-H1 is GYTFASYW (SEQ ID NO: 7). The amino acid sequence of CDR-H2 is IDPYDSET (SEQ ID NO: 8). The amino acid sequence of CDR-H3 is ARLGRG-PFAY (SEQ ID NO: 9).

The nucleic acid sequence encoding the mature form (signal peptide removed) of Ab 778.17 heavy chain is SEQ ID NO: 28:

(SEQ ID NO: 28)
CAGGTCCAACTACAGCAGCCTGGGGCTGAACTGGTGAGGCCTGGGACT

TCAGTGAAGCTGTCCTGCAAGGCTTCTGGCTACACGTTCGCCAGCTAC

TGGATGAACTGGGTTAGTCAGAGGCCTGAGCAAGGCCTTGAGTGGATT

GGAAGGATCGATCCTTACGATAGTGAAACTCACTACAATCAAAAGTTC

AAGGACAAGGCCATATTGACTGTAGACAAATCCTCCAGCACAGCCTAC

ATACAACTCAACAGCCTGACATCTGAGGACTCTGCGGTCTATTACTGT

GCAAGATTAGGGAGGGGGCCTTTTGCTTACTGGGGCCAAGGGACTCTG

GTCACTGTCTCTGCAGCCAAAACGACACCCCCATCTGTCTAT.

In one embodiment, the integrin alpha-2 binding agent is Ab 774.3 or an integrin alpha-2-binding fragment thereof. Ab 774.3 is a mouse antibody that binds to integrin alpha-2. The amino acid sequence of the mature form (signal peptide removed) of Ab 774.3 light chain is shown in SEQ ID NO: 24: GYSWCSITCKASQDVGTAVAWYQQK-PGQSPKLLIYWAATRHTGVPDRFAGSGSGT DFTLTISNVQSEDLADYFCQQYSTYPLT-FGAGTKLELKRADAAPTVS (SEQ ID NO: 24). The amino acid sequence of CDR-L1 is QDVGTA (SEQ ID NO: 16). The amino acid sequence of CDR-L2 is WAA (SEQ ID NO: 17). The amino acid sequence of CDR-L3 is QQYSTY-PLT (SEQ ID NO: 18).

The nucleic acid sequence encoding the mature form (signal peptide removed) of Ab 774.3 light chain is SEQ ID NO: 31:

(SEQ ID NO: 31)
GGATACAGTTGGTGCAGCATCACCTGCAAGGCCAGTCAGGATGTGGGT

ACTGCTGTCGCCTGGTATCAACAGAAACCAGGGCAATCTCCTAAATTA

CTGATTTACTGGGCAGCCACCCGGCACACTGGAGTCCCTGATCGCTTC

GCAGGCAGTGGATCTGGGACAGACTTCACTCTCACCATTAGCAATGTG

CAGTCTGAAGACTTGGCAGATTATTTCTGTCAACAATATAGCACCTAT

CCACTCACGTTCGGTGCTGGGACCAAGCTGGAGCTGAAACGGGCTGAT

GCTGCACCAACTGTATCC.

The amino acid sequence of the mature form (signal peptide removed) of mAb 774.3 heavy chain is shown in SEQ ID NO: 23: EVQLQESGPGLVQPSQSLSITCTVS-GLSLTNYGVHWVRQSPGKGLEWLGVIWSGGNT DYNAAFISRLNIKKDNSKNQVFFK-MNSLQVNDTVGSRNLSHRLLRESVLPKC (SEQ ID NO: 23). The amino acid sequence of CDR-H1 is GLSLTNYG (SEQ ID NO: 13). The amino acid sequence of CDR-H2 is IWSGGNT (SEQ ID NO: 14). The amino acid sequence of CDR-H3 is LSHRLL (SEQ ID NO: 15).

The nucleic acid sequence encoding the mature form (signal peptide removed) of Ab 774.3 heavy chain is SEQ ID NO: 30:

(SEQ ID NO: 30)
GAGGTACAGCTGCAGGAGTCAGGACCTGGCCTAGTGCAGCCCTCACAG

AGCCTGTCCATCACCTGCACAGTCTCTGGTTTGTCATTAACTAATTAT

GGTGTCCACTGGGTTCGCCAGTCTCCAGGAAAGGGTCTGGAGTGGCTG

GGAGTGATTTGGAGTGGTGGAAACACAGACTATAACGCAGCTTTCATA

TCCAGACTGAACATCAAGAAGGACAATTCCAAGAACCAAGTCTTCTTT

AAAATGAACAGTCTGCAAGTTAATGACACAGTCGGGTCAAGGAACCTC

AGTCACCGTCTCCTCAGAGAGTCAGTCCTTCCCAAATGT.

Epitopes Bound by Integrin Alpha-2 Binding Agents

The invention further provides an integrin alpha-2 binding agent that binds peptides having the amino acid sequence of SEQ ID NO: 32 and/or SEQ ID NO: 33 (e.g., peptide(s) comprising (or consisting of) the amino acid sequence of SEQ ID NO: 32 and SEQ ID NO: 33). Integrin alpha-2 is an 1183 amino acid protein (Genbank accession number AAM34795.1). In addition to other structural features, the ligand-binding domain of integrin alpha-2 is the αI domain, homologous to the βI domain found in all the integrin β-subunits. Epitope mapping with a peptide microarray consisting of a set of 15-mer peptides overlapping by 10 residues taken from the human alpha-2 integrin subunit revealed that Ab 770.8, Ab 774.3, and Ab 778.17 recognized peptides of SEQ ID NO: 32 (YANNPRVVFNLNTYK) and SEQ ID NO: 33 (AIASIPTERYFFNVS). These peptides map to the I domain of the alpha-2 integrin and further comprise the junction of beta sheet βC and βF within the alpha-2 integrin I domain crystal structure. The I domain of integrin alpha-2 interacts with type 1 collagen found in the extracellular matrix.

Ab 770.8, Ab 774.3, and Ab 778.17 are exemplary and representative of a group of antibodies that bind to peptides comprising the amino acid sequences of SEQ ID NO: 32 and SEQ ID NO: 33. Antibodies (or fragments thereof) having this characteristic binding pattern may or may not share amino acid sequence in one or more regions of the antibody molecule. Antibody similarity is determined functionally such as by the ability to bind to the epitopes defined by SEQ ID NO: 32 and/or SEQ ID NO: 33. Antibodies that exhibit a binding pattern similar or identical to that of antibody Ab 770.8, Ab 774.3, and Ab 778.17 are included in the invention. By "similar to," it is meant, for example, the antibody will bind peptides comprising the amino acid sequence of SEQ ID NO: 32 and/or SEQ ID NO: 33, whereby preincubation of the antibody with integrin alpha-2 or an integrin alpha-2 peptide fragment will result in at least a 50% (e.g., at least 60%, at least 70%, at least 80%, or at least 90%) reduction in the antibody's binding to integrin alpha-2 that would otherwise occur in the absence of the preincubation.

Materials and Methods for Producing Antibodies and Fragments Thereof

In various embodiments, the integrin alpha-2 binding agent is an antibody or integrin alpha-2-binding fragment thereof. Antibodies according to the invention are obtained by any suitable method, such as (but not limited to) immunization with whole tumor cells comprising integrin alpha-2 and collection of antibodies, recombinant techniques, or screening libraries of antibodies or antibody fragments using integrin alpha-2 extracellular domain epitopes. Monoclonal antibodies of the invention are generated using a variety of known techniques (see, for example, Coligan et al. (eds.), *Current Protocols in Immunology*, 1:2.5.12.6.7 (John Wiley & Sons 1991); *Monoclonal Antibodies, Hybridomas: A New Dimension in Biological Analyses*, Plenum Press, Kennett, McKearn, and Bechtol (eds.) (1980); *Antibodies: A Laboratory Manual*, Harlow and Lane (eds.), Cold Spring Harbor Laboratory Press (1988); and Picksley et al., "Production of monoclonal antibodies against proteins expressed in *E. coli*," in *DNA Cloning 2: Expression Systems*, 2nd Edition, Glover et al. (eds.), page 93 (Oxford University Press 1995)). One exemplary technique for generating monoclonal antibodies comprises immunizing an animal with an integrin alpha-2 antigen and generating a hybridoma from spleen cells taken from the animal. The invention provides a hybridoma that produces the inventive monoclonal antibody or antibody fragment.

Likewise, human antibodies are generated by any of a number of techniques including, but not limited to, Epstein Barr Virus (EBV) transformation of human peripheral blood cells (e.g., containing B lymphocytes), in vitro immunization of human B cells, fusion of spleen cells from immunized transgenic mice carrying inserted human immunoglobulin genes, isolation from human immunoglobulin V region phage libraries, or other procedures as known in the art and based on the disclosure herein. Methods for obtaining human antibodies from transgenic animals are further described, for example, in Bruggemann et al., *Curr. Opin. Biotechnol.*, 8: 455 58, 1997; Jakobovits et al., *Ann. N.Y. Acad. Sci.*, 764: 525 35, 1995; Green et al., *Nature Genet.*, 7: 13-21, 1994; Lonberg et al., *Nature*, 368: 856-859, 1994; Taylor et al., *Int. Immun.* 6: 579-591, 1994; and U.S. Pat. No. 5,877,397.

For example, human antibodies are obtained from transgenic animals that have been engineered to produce specific human antibodies in response to antigenic challenge. For example, International Patent Publication No. WO 98/24893 discloses transgenic animals having a human Ig locus, wherein the animals do not produce functional endogenous immunoglobulins due to the inactivation of endogenous heavy and light chain loci. Transgenic non-primate mammalian hosts capable of mounting an immune response to an immunogen, wherein the antibodies have primate constant and/or variable regions, and wherein the endogenous immunoglobulin encoding loci are substituted or inactivated, also have been described. International Patent Publication No. WO 96/30498 discloses the use of the Cre/Lox system to modify the immunoglobulin locus in a mammal, such as to replace all or a portion of the constant or variable region to form a modified antibody molecule. International Patent Publication No. WO 94/02602 discloses non-human mammalian hosts having inactivated endogenous Ig loci and functional human Ig loci. U.S. Pat. No. 5,939,598 discloses methods of making transgenic mice in which the mice lack endogenous heavy chains, and express an exogenous immunoglobulin locus comprising one or more xenogeneic constant regions. Using a transgenic animal, such as a transgenic animal described herein, an immune response can be produced to a selected antigenic molecule, and antibody producing cells can be removed from the animal and used to produce hybridomas that secrete human-derived monoclonal antibodies. Immunization protocols, adjuvants, and the like are known in the art, and are used in immunization of, for example, a transgenic mouse as described in International Patent Publication No. WO 96/33735. The monoclonal antibodies can be tested for the ability to inhibit or neutralize the biological activity or physiological effect of the corresponding protein.

Humanized antibodies such as those described herein can be produced using techniques known to those skilled in the art (Zhang et al., *Molecular Immunology*, 42 (12): 1445-1451, 2005; Hwang et al., *Methods*, 36 (1): 35-42, 2005; Dall'Acqua et al., *Methods*, 36 (1): 43-60, 2005; Clark, *Immunology Today*, 21 (8): 397-402, 2000, and U.S. Pat. Nos. 6,180,370; 6,054,927; 5,869,619; 5,861,155; 5,712,120; and 4,816,567, all of which are all hereby expressly incorporated herein by reference).

The invention further provides materials for generating integrin alpha-2 binding agents, e.g., integrin alpha-2-binding antibodies and fragments thereof. For example, the invention provides an isolated cell (e.g., a hybridoma) that produces the inventive binding agent (e.g., antibody or antibody fragment). In this regard, the invention includes a cell (e.g., an isolated cell) that produces Ab 770.8, Ab 778.17, or Ab 774.3. The invention further includes a polynucleotide comprising a nucleic acid sequence encoding the inventive integrin alpha-2 binding agent (e.g., antibody or antibody fragment). In various aspects, the polynucleotide is an isolated and/or recombinant polynucleotide. In various aspects of the invention, the isolated polynucleotide comprises a nucleotide sequence that encodes an antibody heavy chain variable region (VH) and/or an antibody light chain variable region ($V_L$), wherein the $V_H$ and the $V_L$ comprise complementarity determining regions (CDRs) identical to mAb 770.8, mAb 778.17, or mAb 774.3 CDRs. The polynucleotide optionally comprises the nucleic acid sequence of SEQ ID NOs: 26-31.

In a related embodiment, the invention provides a vector (e.g., an expression vector) comprising a polynucleotide of the invention to direct expression of the polynucleotide in a suitable host cell. Such vectors are useful, e.g., for amplifying the polynucleotides in host cells to create useful quantities thereof, and for expressing peptides, such as antibodies or antibody fragments, using recombinant techniques. Vectors also are useful in "gene therapy" treatment regimens, wherein, for example, a polynucleotide encoding an integrin alpha-2 binding agent (e.g., antibody or fragment thereof) is introduced into a subject suffering from or at risk of suffering from, e.g., cancer(s), fibrosis, or angiogenesis in a form that causes cells in the subject to express the binding agent in vivo.

In preferred embodiments, the vector is an expression vector wherein the polynucleotide of the invention is operatively linked to a polynucleotide comprising an expression control sequence. Autonomously replicating recombinant expression constructs such as plasmid and viral DNA vectors incorporating polynucleotides of the invention are specifically contemplated. Expression control DNA sequences include promoters, enhancers, and operators, and are generally selected based on the expression systems in which the expression construct is to be utilized. Preferred promoter and enhancer sequences are generally selected for the ability to increase gene expression, while operator sequences are generally selected for the ability to regulate gene expression. Expression constructs of the invention may also include sequences encoding one or more selectable markers that permit identification of host cells bearing the construct. Expression constructs may also include sequences that facilitate, and preferably promote, homologous recombination in a host cell. Preferred expression constructs of the invention also include sequences necessary for replication in a host cell.

Exemplary expression control sequences include promoter/enhancer sequences, e.g., cytomegalovirus promoter/enhancer (Lehner et al., *J. Clin. Microbiol.*, 29: 2494-2502, 1991; Boshart et al., *Cell*, 41: 521-530, 1985); Rous sarcoma virus promoter (Davis et al., *Hum. Gene Ther.*, 4: 151, 1993); Tie promoter (Korhonen et al., *Blood*, 86 (5): 1828-1835, 1995); simian virus 40 promoter; DRA (downregulated in adenoma; Alrefai et al., *Am. J. Physiol. Gastrointest. Liver Physiol.*, 293: G923-G934, 2007); MCT1 (monocarboxylate transporter 1; Cuff et al., *Am. J. Physiol. Gastrointet. Liver Physiol.*, G977-G979. 2005); and Math1 (mouse atonal homolog 1; Shroyer et al., *Gastroenterology*, 132: 2477-2478, 2007), for expression in the target mammalian cells, the promoter being operatively linked upstream (i.e., 5') of the polypeptide coding sequence (the disclosures of the cited references is incorporated herein by reference in their entirety and particularly with respect to the discussion of expression control sequences). In another variation, the promoter is an epithelial-specific promoter or endothelial-specific promoter. The polynucleotides of the invention may also optionally include a suitable polyadenylation sequence (e.g., the SV40 or human growth hormone gene polyadenylation sequence) operably linked downstream (i.e., 3') of the polypeptide coding sequence.

If desired, the polynucleotide also optionally comprises a nucleotide sequence encoding a secretory signal peptide fused in frame with the polypeptide sequence. The secretory signal peptide directs secretion of the polypeptide (e.g., antibody) of the invention by the cells that express the polynucleotide, and is cleaved by the cell from the secreted polypeptide. The polynucleotide may further optionally comprise sequences whose only intended function is to facilitate large scale production of the vector, e.g., in bacteria, such as a bacterial origin of replication and a sequence encoding a selectable marker. However, if the vector is administered to an animal, such extraneous sequences are preferably at least partially cleaved. One can manufacture and administer polynucleotides for gene therapy using procedures that have been described in the literature for other transgenes. See, e.g., Isner et al., *Circulation,* 91: 2687-2692, 1995; and Isner et al., *Human Gene Therapy,* 7: 989-1011, 1996; incorporated herein by reference.

In some embodiments, polynucleotides of the invention further comprise additional sequences to facilitate uptake by host cells and expression of the antibody or fragment thereof (and/or any other peptide). In one embodiment, a "naked" transgene encoding an antibody or fragment thereof described herein (i.e., a transgene without a viral, liposomal, or other vector to facilitate transfection) is employed.

Any suitable vector may be used to introduce a polynucleotide that encodes an antibody or fragment thereof into the host. Exemplary vectors that have been described in the literature include replication deficient retroviral vectors, including but not limited to lentivirus vectors (Kim et al., *J. Virol.,* 72 (1): 811-816, 1998; Kingsman & Johnson, *Scrip Magazine,* October, 1998, pp. 43-46); parvoviral vectors, such as adeno-associated viral (AAV) vectors (U.S. Pat. Nos. 5,474,9351; 5,139,941; 5,622,856; 5,658,776; 5,773,289; 5,789,390; 5,834,441; 5,863,541; 5,851,521; 5,252,479; Gnatenko et al., *J. Invest. Med.,* 45: 87-98, 1997); adenoviral (AV) vectors (U.S. Pat. Nos. 5,792,453; 5,824,544; 5,707,618; 5,693,509; 5,670,488; 5,585,362; Quantin et al., Proc. Natl. Acad. Sci. USA, 89: 2581-2584, 1992; Stratford Perricaudet et al., *J. Clin. Invest.,* 90: 626-630, 1992; and Rosenfeld et al., *Cell,* 68: 143-155, 1992); an adenoviral adeno-associated viral chimeric (U.S. Pat. No. 5,856,152) or a vaccinia viral or a herpesviral vector (U.S. Pat. Nos. 5,879,934; 5,849,571; 5,830,727; 5,661,033; 5,328,688); Lipofectin mediated gene transfer (BRL); liposomal vectors (U.S. Pat. No. 5,631,237); and combinations thereof. All of the foregoing documents are incorporated herein by reference in their entirety and particularly with respect to their discussion of expression vectors. Any of these expression vectors can be prepared using standard recombinant DNA techniques described in, e.g., Sambrook et al., *Molecular Cloning, a Laboratory Manual,* 2d edition, Cold Spring Harbor Press, Cold Spring Harbor, N.Y. (1989), and Ausubel et al., *Current Protocols in Molecular Biology,* Greene Publishing Associates and John Wiley & Sons, New York, N.Y. (1994). Optionally, the viral vector is rendered replication-deficient by, e.g., deleting or disrupting select genes required for viral replication.

Other non-viral delivery mechanisms contemplated include calcium phosphate precipitation (Graham and Van Der Eb, *Virology,* 52: 456-467, 1973; Chen and Okayama, *Mol. Cell Biol.,* 7: 2745-2752, 1987; Rippe et al., *Mol. Cell Biol.,* 10: 689-695, 1990) DEAE-dextran (Gopal, *Mol. Cell Biol.,* 5: 1188-1190, 1985), electroporation (Tur-Kaspa et al., *Mol. Cell Biol.,* 6: 716-718, 1986; Potter et al., *Proc. Nat. Acad. Sci. USA,* 81: 7161-7165, 1984), direct microinjection (Harland and Weintraub, *J. Cell Biol.,* 101: 1094-1099, 1985, DNA-loaded liposomes (Nicolau and Sene, *Biochim. Biophys. Acta,* 721: 185-190, 1982; Fraley et al., *Proc. Natl. Acad. Sci. USA,* 76: 3348-3352, 1979; Felgner, *Sci Am.,* 276 (6): 102-6, 1997; Felgner, *Hum Gene Ther.,* 7 (15): 1791-3, 1996), cell sonication (Fechheimer et al., *Proc. Natl. Acad. Sci. USA,* 84: 8463-8467, 1987), gene bombardment using high velocity microprojectiles (Yang et al., *Proc. Natl. Acad. Sci USA,* 87: 9568-9572, 1990), and receptor-mediated transfection (Wu and Wu, *J. Biol. Chem.,* 262: 4429-4432, 1987; Wu and Wu, *Biochemistry,* 27: 887-892, 1988; Wu and Wu, *Adv. Drug Delivery Rev.,* 12: 159-167, 1993).

The expression vector (or the antibody or fragment thereof discussed herein) may be entrapped in a liposome. See, e.g., Ghosh and Bachhawat, In: *Liver diseases, targeted diagnosis and therapy using specific receptors and ligands,* Wu G, Wu C ed., New York: Marcel Dekker, pp. 87-104 (1991); Radler et al., *Science,* 275 (5301): 810-814, 1997). Also contemplated in the invention are various commercial approaches involving "lipofection" technology. In certain embodiments of the invention, the liposome may be complexed with a hemagglutinating virus (HVJ). This has been shown to facilitate fusion with the cell membrane and promote cell entry of liposome-encapsulated DNA (Kaneda et al., *Science,* 243: 375-378, 1989). In other embodiments, the liposome is complexed or employed in conjunction with nuclear nonhistone chromosomal proteins (HMG-1) (Kato et al., *J. Biol. Chem.,* 266: 3361-3364, 1991). In yet further embodiments, the liposome are complexed or employed in conjunction with both HVJ and HMG-1. Such expression constructs have been successfully employed in transfer and expression of nucleic acid in vitro and in vivo. In some variations of the invention, an integrin alpha-2-targeting moiety, such as an integrin alpha-2 antibody or fragment, is included in the liposome to target the liposome to cells (such as cancer cells) expressing integrin alpha-2 on their surface.

The invention further provides a cell that comprises the polynucleotide or the vector, e.g., the cell is transformed or transfected with a polynucleotide encoding the integrin alpha-2 binding agent or a vector comprising the polynucleotide. In certain aspects of the invention, the cell expresses an anti-integrin alpha-2 antibody or antibody fragment containing one or more CDRs having at least 75% identity to the CDRs of Ab 770.8, Ab 778.17, or Ab 774.3. In various embodiments, the cell expresses an anti-integrin alpha-2 antibody or antibody fragment containing the $V_H$ and the $V_L$ comprising CDRs identical to those of Ab 770.8, Ab 778.17, or Ab 774.3. The cell may be a prokaryotic cell, such as *Escherichia coli* (see, e.g., Pluckthun et al., *Methods Enzymol.,* 178: 497-515, 1989), or a eukaryotic host cell, such as an animal cell (e.g., a myeloma cell, Chinese Hamster Ovary cell, or hybridoma cell), yeast (e.g., *Saccharomyces cerevisiae*), or a plant cell (e.g., a tobacco, corn, soybean, or rice cell). Use of mammalian host cells is expected to provide for such translational modifications (e.g., glycosylation, truncation, lipidation, and phosphorylation) that may be desirable to confer optimal biological activity on recombinant expression products. Similarly, the invention embraces polypeptides (e.g., antibodies) that are glycosylated or non-glycosylated and/or have been covalently modified to include one or more water soluble polymer attachments such as polyethylene glycol, polyoxyethylene glycol, or polypropylene glycol.

Methods for introducing DNA into the host cell, which are well known and routinely practiced in the art, include transformation, transfection, electroporation, nuclear injection, or fusion with carriers such as liposomes, micelles, ghost cells, and protoplasts. As stated above, such host cells are useful for amplifying the polynucleotides and also for expressing the polypeptides of the invention encoded by the polynucleotide. In this regard, the invention provides a process for the production of an integrin alpha-2 binding agent, comprising culturing the host cell described herein and isolating the integrin alpha-2 binding agent. Transferring a naked DNA expression construct into cells can be accomplished using particle bombardment, which depends on the ability to accelerate DNA coated microprojectiles to a high velocity allowing them to pierce cell membranes and enter cells without killing them (Klein et al., *Nature,* 327: 70-73, 1987). Several devices for accelerating small particles have been developed. One such device relies on a high voltage discharge to generate an electrical current, which in turn provides the motive force (Yang et al., *Proc. Natl. Acad. Sci USA,* 87: 9568-9572, 1990). The microprojectiles used have consisted of biologically inert substances such as tungsten or gold beads. The host cell may be isolated and/or purified. The host cell also may be a cell transformed in vivo to cause transient or permanent expression of the polypeptide in vivo. The host cell may also be an isolated cell transformed ex vivo and introduced post-transformation, e.g., to produce the polypeptide in vivo for therapeutic purposes. The definition of host cell explicitly excludes a transgenic human being.

Particular methods for producing antibodies from polynucleotides are generally well-known and routinely used. For example, basic molecular biology procedures are described by Maniatis et al., *Molecular Cloning, A Laboratory Manual*, 2nd ed., Cold Spring Harbor Laboratory, New York, 1989 (see also Maniatis et al, 3rd ed., Cold Spring Harbor Laboratory, New York, 2001). Additionally, numerous publications describe techniques suitable for the preparation of antibodies by manipulation of DNA, creation of expression vectors, and transformation and culture of appropriate cells (see, e.g., Mountain and Adair, Chapter 1 in *Biotechnology and Genetic Engineering Reviews*, Tombs ed., Intercept, Andover, UK, 1992); and *Current Protocols in Molecular Biology*, Ausubel ed., Wiley Interscience, New York, 1999).

In one aspect, the invention provides a method of producing an antibody, the method comprising (a) propagating cancer cells in a three-dimensional matrix (i.e., a three-dimensional cell culture gel); (b) immunizing a mammal with the propagated cancer cells; and (c) isolating an antibody from the immunized mammal. Cellular processes are modulated by the compositional and mechanical properties of a surrounding three-dimensional extracellular matrix (ECM). Thus, the three-dimensional matrix preferably comprises components typically found in the extracellular matrix, e.g., various combinations of collagen, fibrin, elastin, proteoglycans, and structural glycoproteins. Any cancer cell type capable of proliferating in in vitro three-dimensional matrix may be utilized. Optionally, the method further comprises (d) testing the antibody for anti-cancer activity. Examples of assays for evaluating the activity of an integrin alpha-2 binding agent for anti-cancer activity (e.g., inhibition of cancer cell proliferation) include, but are not limited to, ELISA assays and three-dimensional cell proliferation assays. The method optionally includes collecting spleen cells from the immunized animal and generating a hybridoma that produces an anti-integrin alpha-2 antibody or antibody fragment. In various embodiments, the antibody is a monoclonal antibody.

The invention further includes a method of identifying an agent that inhibits cancer cell proliferation. The method comprises performing a competition assay with a candidate agent and an antibody selected from the group consisting of Ab 770.8, Ab 778.17, and Ab 774.3 or an antigen-binding fragment of any of the foregoing. The method further comprises isolating a candidate agent that is blocked from binding an integrin alpha-2 polypeptide of SEQ ID NO: 25 (or portion thereof) by Ab 770.8, Ab 778.17, Ab 774.3, or an antigen-binding fragment of any of the foregoing. Alternatively or in addition, the method comprises isolating a candidate agent that blocks the binding of Ab 770.8, Ab 778.17, Ab 774.3, or an antigen-binding fragment of any of the foregoing to integrin alpha-2. Any candidate agent is suitable for screening in the context of the inventive method; in one aspect, the agent is an antibody or fragment thereof. The method is amenable to high-throughput screening and allow for faster and cheaper identification of candidate therapeutics compared to existing techniques. Moreover, the use of an in vitro three-dimensional matrix recapitulates cell function and behavior in vivo such that the propagated cancer cells are more likely to display antigens that would be displayed in vivo, allowing for unbiased discovery of novel cancer drug targets.

Inhibiting Cancer Cell Proliferation and Treating Cancer

In various embodiments of the invention, the integrin alpha-2 binding agent inhibits proliferation of cancer cells in three-dimensional cell culture. For example, in one aspect, the integrin alpha-2 binding agent inhibits proliferation of cancer cells in a three-dimensional cell culture when the agent is present at a concentration of about 50 nM to about 500 nM (e.g., about 100 nM). Cancer cells include, but are not limited to, breast cancer cells, bladder cancer cells, melanoma cells, prostate cancer cells, mesothelioma cells, lung cancer cells, testicular cancer cells, thyroid cancer cells, squamous cell carcinoma cells, glioblastoma cells, neuroblastoma cells, uterine cancer cells, colorectal cancer cells, and pancreatic cancer cells.

The invention includes a method of inhibiting proliferation of cancer cells. The method comprises contacting cancer cells with an amount of an integrin alpha-2 binding agent (such as an integrin alpha-2 binding agent described herein) effective to inhibit proliferation of the cancer cells. In various embodiments, the invention includes contacting cancer cells with an integrin alpha-2 binding agent (e.g., an antibody or fragment thereof) that competes for binding with Ab 770.8, Ab 778.17, or Ab 774.3 to human integrin alpha-2 and/or binds the region of integrin alpha-2 recognized by Ab 770.8, Ab 778.17, or Ab 774.3, and inhibits cancer cell proliferation. In some embodiments, the cancer cells are in a subject, and the contacting comprises administering the integrin alpha-2 binding agent to the subject. It will be understood that the polynucleotide, vector, and cell of the invention can be used in methods of inhibiting cancer cell proliferation in vitro and in vivo (e.g., in a method of treating cancer in a subject).

A method of modulating tumor growth in a subject also is provided. The method comprises administering to the subject a composition comprising an integrin alpha-2 binding agent in an amount effective to modulate tumor growth in the subject. "Tumor" refers to any neoplastic cell growth or proliferation, whether malignant or benign, and to all pre-cancerous and cancerous cells and tissues. The terms "cancer" and "cancerous" refer to or describe the physiological condition in mammals that is typically characterized by unregulated cell growth. Examples of cancer include, but are not limited to, carcinoma, lymphoma, blastoma, sarcoma, and leukemia. Examples of cancers include breast cancer, prostate cancer, colon cancer, squamous cell cancer, lung cancer (e.g., small-cell lung cancer or non-small cell lung cancer), melanoma, mesothelioma, gastrointestinal cancer, pancreatic cancer, glioblastoma, neuroblastoma, cervical cancer, ovarian cancer, liver cancer, bladder cancer, hepatoma, colorectal cancer, endometrial carcinoma, salivary gland carcinoma, kidney cancer, liver cancer, vulval cancer, thyroid cancer, esophageal cancer, hepatic carcinoma and various types of head and neck cancer. "Metastatic cancer" is cancer that has the potential to, or has begun to, spread to other areas of the body. A variety of cancers can metastasize, but the most common metastasizing cancers are breast, lung, renal, multiple myeloma, thyroid and prostate. By way of example, other cancers that have the potential to metastasize include, but are not limited to, adenocarcinoma; blood cell malignancies, including leukemia and lymphoma; head and neck cancers; gastrointestinal cancers, including esophageal cancer, stomach cancer, colon cancer, intestinal cancer, colorectal cancer, rectal cancer, pancreatic cancer, liver cancer, cancer of the bile duct or gall bladder; malignancies of the female genital tract, including ovarian carcinoma, uterine endometrial cancers, vaginal cancer, and cervical cancer; bladder cancer; testicular cancer; brain cancer, including neuroblastoma and glioma; sarcoma; osteosarcoma; and skin cancer, including malignant melanoma and squamous cell cancer. In various embodiments, the invention includes a method of treating cancer by administering an integrin alpha-2 binding agent to a subject in need thereof.

"Inhibiting" cancer cell proliferation does not require a 100% prevention of proliferation. Any reduction in the rate of proliferation is contemplated. Similarly, "modulating" tumor growth refers to reducing the size of the tumor, slowing tumor growth, or inhibiting an increase in the size of an existing tumor. Complete abolition of a tumor is not required; any decrease in tumor size or slowing of tumor growth constitutes a beneficial biological effect in a subject. In this regard, the invention reduces cancer cell proliferation by, e.g., at least about 5%, at least about 10% or at least about 20% compared to levels of proliferation observed in the absence of the inventive method (e.g., in a biologically-matched control subject or specimen that is not exposed to the agent of the inventive method). The effect is detected by, for example, a reduction in tumor size, a decrease or maintenance of the levels of cancer markers, or reduction or maintenance of a cancer cell population. In some embodiments, proliferation is reduced by at least about 30%, at least about 40%, at least about 50%, or at least about 60%. In some embodiments, the inventive method inhibits proliferation by at least about 70%, at least about 80%, at least about 90%, or more (about 100%) compared to proliferation in the absence of the agent of the inventive method.

Additionally, the integrin alpha-2 binding agents may be used to alleviate or reduce side effects associated with cancer such as, for example, bone deterioration, vertebral collapse, and paralysis. In one aspect, the subject suffers from or is at risk of suffering from bone metastases and the integrin alpha-2 binding agent is administered in an amount to reduce deterioration of surrounding bone. Accordingly, in some aspects, the integrin alpha-2 binding agent prevents bone deterioration due to bone metastases but does not reduce cancer cell proliferation. However, in other aspects, the integrin alpha-2 binding agent both prevents bone deterioration due to bone metastases and reduces cancer cell proliferation. In general, the effect on cancer cell proliferation (i.e., inhibition of proliferation or no effect on proliferation) depends on the microenvironment of a particular metastasis. Without wishing to be bound by any particular theory, proliferation of metastases located in microenvironments with substantial amounts of type 1 collagen is inhibited. In contrast, proliferation of metastases located in microenvironments lacking substantial amounts of type 1 collagen may not be inhibited, yet bone deterioration in the vicinity of the metastasis is reduced or prevented.

Inhibiting Angiogenesis

A method of inhibiting angiogenesis in a subject is also provided. The method comprises administering to the subject a composition comprising an integrin alpha-2 binding agent in an amount effective to inhibit angiogenesis in the subject.

Angiogenesis plays an important role in tumor formation and growth. The development of a blood vessel system to deliver nutrients to the developing tumor is critical for tumorigenesis. Tumor angiogenesis involves increased endothelial cell proliferation and migration, and tube formation into the tumor mass. During angiogenesis, endothelial cells become activated, degrade local basement membrane, and the vessel begins to "sprout" with migrating tip cells leading a column of proliferating stalk cells. These blood vessel sprouts eventually form lumens and develop into a network. The newly formed vessels are stabilized by the synthesis of a new basement membrane and the recruitment of supporting cells such as pericytes and vascular smooth muscle cells. These angiogenic steps involve changes in endothelial or pericyte adhesion. Abnormal angiogenesis also is associated with a myriad of other diseases or disorders, including ocular neovascular disease, arthritis, hemangiomas, and skin disorders, such as psoriasis. Integrins play a role in angiogenesis.

The term "angiogenesis" refers to all processes that contribute to the growth of new blood vessels from pre-existing vessels, in particular but not limited to new tumor-supplying blood vessels. These processes include multiple cellular events such as proliferation, survival, migration and sprouting of vascular endothelial cells, attraction and migration of pericytes as well as basal membrane formation for vessel stabilization, vessel perfusion, or secretion of angiogenic factors by stromal or neoplastic cells.

"Inhibiting" angiogenesis does not require a 100% prevention of angiogenesis. Any reduction in the rate of angiogenesis is contemplated. Any decrease in angiogenesis constitutes a beneficial biological effect in a subject. In this regard, the invention reduces angiogenesis by, e.g., at least about 5%, at least about 10% or at least about 20% compared to levels of angiogenesis observed in the absence of the inventive method (e.g., in a biologically-matched control subject or specimen that is not exposed to the agent of the inventive method). The effect is detected by, for example, a decrease in blood vessel formation, a reduction in tumor size, a decrease or maintenance of the levels of cancer markers, or reduction or maintenance of a cancer cell population. Any suitable animal angiogenesis model may be used including, but not limited to a mouse or rabbit ear model of neovascularization (Frank et al. 1994. *Microsurgery*, 15 (6): 399-404), an animal model of rheumatoid arthritis (Haas et al. 2007. *Arthritis Rheum.*, 56 (8): 2535-48), or an in vivo cancer model, such as a mouse melanoma metastasis model (Lee et al. 2006. *Cancer Chemother. Pharmacol.*, 57 (6): 761-71) or a canine model of human invasive urinary bladder cancer (Mohammed et al. 2003. *Mol. Cancer Ther.*, 2 (2): 183-188). Doppler imaging and magnetic resonance imaging detect blood flow or vascularization changes in tissue (see, e.g., Taylor. 2002. *Arthritis Res.*, 4 (suppl. 3): S99-S107), and microscopic examination of tissue biopsies detects changes in vessel number or quality. Perfusion computed tomography ("perfusion CT") (Miles et al. 1998. *Brit. J. Radiol.*, 71: 276-281) and dynamic contrast enhanced magnetic resonance imaging (MRI) (Hathout et al. 2007. *Transpl. Int.*, 20 (12): 1059-1065) also are effective in evaluating neovascularization. Ocular neovascularization can be detected using fluorecein angiography, color Doppler imaging, and by clinical examination. In some embodiments, angiogenesis is reduced by at least about 30%, at least about 40%, at least about 50%, or at least about 60%. In some embodiments, the inventive method inhibits angiogenesis by at least about 70%, at least about 80%, at least about 90%, or more (about 100%) compared to angiogenesis in the absence of the integrin alpha-2 binding agent.

Inhibiting Fibrosis

A method of treating a fibrotic disorder in a subject is also provided. The method comprises administering to the subject a composition comprising an integrin alpha-2 binding agent in an amount effective to treat the fibrotic disorder in the subject.

The process of tissue repair as a part of wound healing involves two phases. The first phase is the regenerative phase, in which injured cells are replaced by cells of the same type. The second phase is the formation of fibrous tissues, also called fibroplasia or fibrosis, in which connective tissue replaces normal parenchymal tissues. The tissue repair process can become pathogenic if the fibrosis phase continues unchecked, leading to extensive tissue remodeling and the formation of permanent scar tissue. Major organ fibrotic disorders include interstitial lung disease (ILD) (characterized by pulmonary inflammation and fibrosis), liver cirrhosis, liver fibrosis resulting from chronic hepatitis B or C infection, kidney disease, heart disease, and eye diseases (including macular degeneration and retinal and vitreal retinopathy). Fibroproliferative disorders also include systemic and local scleroderma, keloids and hypertrophic scars, atherosclerosis, and restenosis. Additional fibroproliferative diseases include excessive scarring resulting from surgery, chemotherapeutic drug-induced fibrosis, radiation-induced fibrosis, and injuries and burns. Integrin alpha-2 has been shown to have a role in fibrosis via interactions with Type I collagen.

In some aspects of the invention, the fibrotic disorder is selected from the group consisting of chronic kidney disease, chronic liver disease, lung fibrosis, systemic sclerosis, organ transplant fibrosis, endomyocardial fibrosis, mediastinal fibrosis, myelofibrosis, retroperitoneal fibrosis, progressive massive fibrosis, nephrogenic systemic fibrosis, Crohn's Disease, and arthrofibrosis. In specific aspects, the lung fibrosis is idiopathic pulmonary fibrosis. In other aspects, the chronic liver disease is selected from the group consisting of Hepatitis C, cirrhosis, NAFLD, NASH, and primary sclerosing cholanitis.

"Treating" a fibrotic disorder does not require a 100% prevention of fibrosis. Any reduction in the rate of fibrosis is contemplated. Any inhibition of fibrosis, decrease in fibrosis, or reduction in the rate of fibrotic tissue generation constitutes a beneficial biological effect in a subject. In this regard, the invention reduces fibrosis by, e.g., at least about 5%, at least about 10% or at least about 20% compared to levels of fibrosis observed in the absence of the inventive method (e.g., in a biologically-matched control subject or specimen that is not exposed to the agent of the inventive method). In some embodiments, fibrosis is reduced by at least about 30%, at least about 40%, at least about 50%, or at least about 60%. In some embodiments, the inventive method inhibits fibrosis by at least about 70%, at least about 80%, at least about 90%, or more (about 100%) compared to fibrosis in the absence of the agent of the inventive method. The effect is detected by, for example, a decrease in scar tissue or fibrous tissue. The effect can also be detected by improvement of symptoms associate with a particular fibrotic disorder. For example, the treatment of idiopathic pulmonary fibrosis can be monitored by measuring changes in lung volume.

Administration Considerations

A particular administration regimen for a particular subject will depend, in part, upon the agent used, the amount of agent administered, the route of administration, and the cause and extent of any side effects. The amount of agent administered to a subject (e.g., a mammal, such as a human) in accordance with the invention should be sufficient to effect the desired response over a reasonable time frame. In various aspects, the inventive method comprises administering, e.g., from about 0.1 µg/kg to up to about 100 mg/kg or more. In other embodiments, the dosage ranges from about 1 µg/kg up to about 100 mg/kg; or about 5 µg/kg up to about 100 mg/kg; or about 10 µg/kg up to about 100 mg/kg; or about 1 mg/kg up to about 50 mg/kg; or about 2 mg/kg up to about 30 mg/kg; or about 3 mg/kg up to about 25 mg/kg; or about 3 mg/kg up to about 25 mg/kg; or about 5 mg/kg up to about 10 mg/kg; or about 10 mg/kg up to about 20 mg/kg; or about 10 mg/kg up to about 30 mg/kg. Some conditions or disease states require prolonged treatment, which may or may not entail administering doses of integrin alpha-2 binding agent over multiple administrations (e.g., every day, three times a week, once a week, once every two weeks, or once every month for a treatment period of three days, seven days, two weeks, three weeks, one month, three months, six months, nine months, 12 months, 15 months, 18 months, 21 months, two years, or more).

Suitable methods of administering a physiologically-acceptable composition, such as a pharmaceutical composition comprising the integrin alpha-2 binding agent, are well known in the art. Although more than one route can be used to administer an agent, a particular route can provide a more immediate and more effective reaction than another route. Depending on the circumstances, a pharmaceutical composition comprising the integrin alpha-2 binding agent is applied or instilled into body cavities, absorbed through the skin or mucous membranes, ingested, inhaled, and/or introduced into circulation. For example, in certain circumstances, it will be desirable to deliver a pharmaceutical composition comprising the agent orally, through injection by intravenous, subcutaneous, intraperitoneal, intracerebral (intra-parenchymal), intracerebroventricular, intramuscular, intra-ocular, intraarterial, intraportal, intralesional, intramedullary, intrathecal, intraventricular, transdermal, subcutaneous, intraperitoneal, intranasal, enteral, topical, sublingual, urethral, vaginal, or rectal means, by sustained release systems, or by implantation devices. If desired, the agent is administered regionally via intraarterial or intravenous administration feeding the region of interest, e.g., via the hepatic artery for delivery to the liver. Alternatively, the composition is administered locally via implantation of a membrane, sponge, or another appropriate material on to which the desired molecule has been absorbed or encapsulated. Where an implantation device is used, the device is, one aspect, implanted into any suitable tissue or organ, and delivery of the desired molecule is, for example, via diffusion, timed-release bolus, or continuous administration. In other aspects, the agent is administered directly to exposed tissue during tumor resection or other surgical procedures. Therapeutic delivery approaches are well known to the skilled artisan, some of which are further described, for example, in U.S. Pat. No. 5,399,363.

The invention includes a composition, such as pharmaceutical composition, comprising the integrin alpha-2 binding agent and a carrier (i.e., vehicle, adjuvant, or diluent). The particular carrier employed is limited only by chemico-physical considerations, such as solubility and lack of reactivity with the binding agent or co-therapy, and by the route of administration. Physiologically acceptable carriers are well-known in the art. Illustrative pharmaceutical forms suitable for injectable use include sterile aqueous solutions or dispersions and sterile powders for the extemporaneous preparation of sterile injectable solutions or dispersions (for example, see U.S. Pat. No. 5,466,468). Injectable formulations are further described in, e.g., *Pharmaceutics and Pharmacy Practice*, J. B. Lippincott Co., Philadelphia. Pa., Banker and Chalmers. eds., pages 238-250 (1982), and *ASHP Handbook on Injectable Drugs*, Toissel, 4th ed., pages 622-630 (1986)). A pharmaceutical composition comprising the integrin alpha-2 binding agent is, in one aspect, placed within containers, along with packaging material that provides instructions regarding the use of such pharmaceutical compositions. Generally, such instructions include a tangible expression describing the reagent concentration, as well as, in certain embodiments, relative amounts of excipient ingredients or diluents (e.g., water, saline or PBS) that may be necessary to reconstitute the pharmaceutical composition.

In various aspects, the method further comprises administering an antineoplastic agent, which may be present in the composition comprising an integrin alpha-2 binding agent or provided in a separate composition using the same or a different route of administration. Antineoplastic therapeutic agents include, but are not limited to, alkylating agents, antibiotics, folate inhibitors, purine analogs, pyrimidine analogs, and radiosensitizing compounds. Specific antineoplastic therapeutic agents illustratively include acivicin, aclarubicin, acodazole, acronine, adozelesin, aldesleukin, alitretinoin, allopurinol, altretamine, ambomycin, ametantrone, amifostine, aminoglutethimide, amsacrine, anastrozole, anthramycin, arsenic trioxide, asparaginase, asperlin, azacitidine, azetepa, azotomycin, batimastat, benzodepa, bicalutamide, bisantrene, bisnafide dimesylate, bizelesin, bleomycin, brequinar, bropirimine, busulfan, cactinomycin, calusterone, capecitabine, caracemide, carbetimer, carboplatin, carmustine, carubicin, carzelesin, cedefingol, celecoxib, chlorambucil, cirolemycin, cisplatin, cladribine, crisnatol mesylate, cyclophosphamide, cytarabine, dacarbazine, dactinomycin, daunorubicin, decitabine, dexormaplatin, dezaguanine, dezaguanine mesylate, diaziquone, docetaxel, doxorubicin, droloxifene, droloxifene, dromostanolone, duazomycin, edatrexate, eflornithine, elsamitrucin, enloplatin, enpromate, epipropidine, epirubicin, erbulozole, esorubicin, estramustine, estramustine, etanidazole, etoposide, etoposide, etoprine, fadrozole, fazarabine, fenretinide, floxuridine, fludarabine, fluorouracil, fluorocitabine, fosquidone, fostriecin, fulvestrant, gemcitabine, gemcitabine, hydroxyurea, idarubicin, ifosfamide, ilmofosine, interleukin II (IL-2, including recombinant interleukin II or rIL2), interferon alpha-2a, interferon alpha-2b, interferon alpha-n1, interferon alpha-n3, interferon beta-1a, interferon gamma-I b, iproplatin, irinotecan, lanreotide, letrozole, leuprolide, liarozole, lometrexol, lomustine, losoxantrone, masoprocol, maytansine, mechlorethamine hydrochloride, megestrol, melengestrol acetate, melphalan, menogaril, mercaptopurine, methotrexate, metoprine, meturedepa, mitindomide, mitocarcin, mitocromin, mitogillin, mitomalcin, mitomycin, nitosper, mitotane, mitoxantrone, mycophenolic acid, nelarabine, nocodazole, nogalamycin, ormnaplatin, oxisuran, paclitaxel, pegaspargase, peliomycin, pentamustine, peplomycin, perfosfamide, pipobroman, piposulfan, piroxantrone hydrochloride, plicamycin, plomestane, porfimer, porfiromycin, prednimustine, procarbazine, puromycin, pyrazofurin, riboprine, rogletimide, safingol, safingol, semustine, simtrazene, sparfosate, sparsomycin, spirogermanium, spiromustine, spiroplatin, streptonigrin, streptozocin, sulofenur, talisomycin, tamoxifen, tecogalan, tegafur, teloxantrone, temoporfin, teniposide, teroxirone, testolactone, thiamiprine, thioguanine, thiotepa, tiazofurin, tirapazamine, topotecan, torernifene, trestolone, triciribine, triethylenemelamine, trimetrexate, triptorelin, tubulozole, uracil mustard, uredepa, vapreotide, verteporlin, vinblastine, vincristine sulfate, vindesine, vinepidine, vinglycinate, vinleurosine, vinorelbine, vinrosidine, vinzolidine, vorozole, zeniplatin, zinostatin, zoledronate, and zorubicin. These and other antineoplastic therapeutic agents are described, for example, in Goodman & Gilman's The Pharmacological Basis of Therapeutics, McGraw-Hill Professional, 10th ed., 2001.

Other exemplary additional therapeutic agents include, but are not limited to, glucocorticoids; kallikrein inhibitors; corticosteroids (e.g., prednisone, methylprednisolone, dexamethasone, or triamcinalone acetinide); anti-inflammatory agents (such as noncorticosteroid anti-inflammatory compounds (e.g., ibuprofen or flubiproben)); vitamins and minerals (e.g., zinc); and anti-oxidants (e.g., carotenoids (such as a xanthophyll carotenoid like zeaxanthin or lutein)). Neutralizing proteins to growth factors, such as a monoclonal antibody that is specific for a given growth factor, e.g., VEGF (for an example, see Aiello et al., *PNAS USA,* 92: 10457-10461 (1995)), or phosphotyrosine (Dhar et al., *Mol. Pharmacol,* 37: 519-525 (1990)), are suitable for co-administration or incorporation into a composition, if desired. Other various additional therapeutic compounds include cytokine modulators, an endothelial cell-specific inhibitor of proliferation (e.g., thrombospondin), an anti-proliferative peptide (e.g., SPARC and proliferin-like peptides), aminoguanidine, an angiotensin-converting enzyme inhibitor (e.g., angiotensin II), an angiogenesis inhibitor, aspirin, and retinoic acid and analogues thereof. The additional therapeutic agent may be a pharmaceutically acceptable salt, ester, amide, hydrate, and/or prodrug of any of these or other therapeutic agents.

EXAMPLES

Example 1

This example describes an exemplary method of generating antibodies to cell surface proteins (e.g., anti-integrin alpha-2 antibodies).

Immunogens were prepared by embedding tumor cells in type I collagen. The type I collagen was prepared from rat or mouse tail tendons and dissolved in 0.2% acetic acid at 2.7 mg/ml. To induce gelling, the collagen solution was mixed with 10×MEM and 0.34N NaOH at a ratio of 8:1:1 at 4° C. MDA-MB-231 cells ($1-5 \times 10^6$) were resuspended in 1 ml of the mixture, then seeded into 12-well plates. Plates were incubated at 37° C. to complete gelling, then culture media added atop of the gel. After four days incubation, cells were harvested by removing the overlayer of media and transferring the collagen gel to a 15 ml centrifuge tube. The gel was washed with PBS, then dissolved by adding 1 ml of Dulbecco's PBS containing collagenase type 3 and incubating at 37° C. Cells were collected by centrifugation and resuspended in PBS for immunization into six-week-old Balb/c female mice.

The immunization protocol typically followed an initial intraperitoneal injection, followed by boosts at two-three week intervals. Once serum titers were acceptable, a final boost was administered and animals were sacrificed four days later. Spleens were removed and standard somatic cell hybridization was performed with the P3X63-Ag8.653 mouse myeloma as fusion partner.

Supernatants from hybridoma clones were assayed in a whole-cell ELISA format. Briefly, cells used in the immunization protocol described above (e.g., MDA-MB-231) were harvested by mechanical scraping from cell culture plates, washed with phosphate-buffered saline (PBS) and re-suspended in PBS containing 1% bovine serum albumin (PBS/BSA) at $10^6$ cells/ml. 100 µl cell suspension ($10^5$ cell/well) was added to wells of 96-well V-bottom PVC plates (Corning) and pelleted by centrifugation at 200 g for five minutes. The supernatant was removed by aspiration or by blotting of upside-down plates on paper towels. The resulting cell pellets were re-suspended in 50 µl of the media supernatant from hybridoma cultures and incubated for one hour at 4° C. Plates were then centrifuged and cells washed twice with 100 µl PBS/BSA. Cells were then resuspended in 50 µl of a horse radish peroxidase (HRP)-conjugated secondary antibody directed against mouse immunoglobulins at manufacturers recommended dilution and incubated for an additional one hour at 4° C. Cells were then washed three times with 100 µl PBS and HRP activity was detected by re-suspending the cells in 50 µl TMB substrate (Thermo Scientific), followed by monitoring absorbance at 450 nm after addition of sulfuric acid.

Cells from active wells were sub-cloned by limiting dilution and re-assayed for activity to ensure the cultures were monoclonal. Active hybridomas were then used to generate ascites fluid by injection into mouse peritoneal cavities. The resulting ascites fluid was cleared of cells and debris by centrifugation at 10,000 g and used as is, or further purified by Melon Gel Purification Resin (Thermo Scientific).

Example 2

This example describes an exemplary assay for evaluating anti-cancer activity of an integrin alpha-2 binding agent. As described further below, Ab 770.8, Ab 774.3 and Ab 778.17 modulate cell shape and inhibit proliferation of cancer cells grown in three-dimensional collagen culture gel.

The ability of an integrin alpha-2 binding agent, Ab 770.8, to inhibit cell proliferation was determined in two- and three-dimensional culture using a hemocytometer. For two-dimensional culture, MDA-MB-431 breast cancer cells were plated at 10,000 cells per well (1 ml/well) in 24-well culture plates using standard growth media or media supplemented with Ab 770.8 ascites fluid. At various times, cells were released from the plastic substrate by treatment with trypsin and enumerated with a hemocytometer.

For evaluation of cell proliferation in three-dimensional collagen gels, MDA-MB-431 cells were embedded in type I collagen ($10^5$ cells/ml) and plated in 24-well plates at 0.5 ml/well. After gelling at 37° C. for 45 minutes, 0.5 ml growth media with or without added Ab 770.8 ascites fluid was added to each well. At various times, cells were harvested by removing the overlayer of media and transferring the collagen gel to a 15 ml centrifuge tube. The gel was washed with PBS, then dissolved by adding 1 ml of Dulbecco's PBS containing 1 mg/ml collagenase type 3 (Worthington) and incubating at 37° C. Following gel dissolution, cells were pelleted, resuspended in PBS and enumerated by hemocytometer.

Cells in two- or three-dimensional culture in the absence of Ab 770.8 ascites fluid exhibited rapid growth, doubling after four days. Ab 770.8 had no effect on cell growth under standard two-dimensional culture conditions. Remarkably, despite having negligible affects in two-dimensional culture, Ab 770.8 prevented the increase in cell number in three-dimensional collagen matrices. The same results were obtained using purified Ab 770.8.

Cell shape and proliferation in three-dimensional culture also was evaluated visually. Type I collagen was prepared from rat tail tendons and dissolved in 0.2% acetic acid at 2.7 mg/ml. To induce gelling, collagen was mixed with 10×MEM and 0.34N NaOH at a ratio of 8:1:1 at 4° C. MDA-MB-231 cells were resuspended at ~700,000 cells/ml in this mixture and plated in 96-well culture plates at 75 μl/well (yielding ~50,000 cells/well). After gelling for 45 min at 37° C., 75 μl culture media (typically DMEM supplemented with 10% fetal bovine serum) containing various dilutions of Ab 770.8 ascites (1:100, 1:300, 1:1000, 1:3000, and 1:10,000), Ab 774.3 (dilutions of 1:100 and 1:500), Ab 778.17 (dilutions of 1:100 and 1:500) culture media with inactive ascites fluid, or culture media alone was added atop of the gel. The MDA-MB-231 cells were incubated in a 37° C. 5% $CO_2$ humidified chamber.

Photomicrographs were taken of the wells using a standard inverted phase contrast microscope fitted with a digital camera to evaluate cell phenotype and proliferation. After two days of culture, untreated cells and cells treated with inactive ascites stretched and had begun proliferating and invading the surrounding collagen matrix. In contrast, cells treated with Ab 770.8, Ab 774.3 and Ab 778.17 at all dilutions tested remained spherical, non-invasive, and non-proliferative.

Additionally, anti-cancer activity of the integrin alpha-2 binding agents, Ab 770.8, Ab 774.3 and Ab 778.17, were evaluated against primary human glioblastoma (GBM) cells. GBM cells were maintained in DMEM/F12 media supplemented with B-27 (Invitrogen), 4 μg/ml heparin, and 20 ng/ml bFGF and EGF in Corning Ultra-Low Attachment tissue culture flasks. Under these conditions, GBM cells typically grow as tumorspheres. For passage, tumorspheres were dissociated into single cells by 10 passages through a 23 gauge hypodermic needle, followed by dilution in supplemented DMEM/F12 media.

Approximately 1000 GBM tumorspheres were embedded in type I collagen gels in 24 well plates (0.5 ml collagen gel/well). After gelling at 37° C. for 45 minutes, 0.5 ml growth media (supplemented with 40 ng/ml bFGF and EGF) or growth media containing 1:1000 dilution Ab 770.8, Ab 774.3 or Ab 778.17 was added. Photomicrographs were taken at various times subsequent to seeding. The cells exhibited a spherical shape initially after seeding. Following four days in culture, cells visibly spread out from the initial spheroid assuming an elongated, stretched morphology, and invaded the collagen matrix. In contrast, cells cultured in the presence of Ab 770.8, Ab 774.3 or Ab 778.18 retained a spheroid shape and failed to invade the surrounding collagen matrix.

The results described above demonstrate that integrin alpha-2 binding agents of the invention (e.g., Ab 770.8, Ab 774.3 and Ab 778.17) inhibit proliferation of multiple cancer cell types in three-dimensional structure.

Example 3

This example describes an exemplary assay for evaluating anti-cancer activity of an integrin alpha-2 binding agent. As detailed below, an integrin alpha-2 binding agent of the invention inhibits cancer cell proliferation and inhibits formation of metastatic sites in a clinically relevant in vivo model.

The embryonic chick xenograft model faithfully recapitulates the metastatic behavior of cancer cells in mouse xenograft models. Conn et al., *Am. J. Pathol.* 175, 1638 (2009); Ota et al., *Proc Natl Acad Sci USA*, 106, 20318 (2009). MDA-MB-231 breast cancer cells expressing red florescent protein RFP (100 μl containing 150,000 cells) were injected into the allantoic vein of 11-day old, immune-incompetent chick embryos. Ab 770.8 (as ascites) was introduced with the cells or added 24 hours after injection of the cells. After six days of incubation, vessel walls were labeled by injection of green fluorescent-labeled isolectin B4 to identify endothelial cells. One hour later, embryos were sacrificed and whole mounts of tissue taken distally from the injection site was evaluated by fluorescent microscopy.

Within chick tissues, blood vessels are surrounded by a dense layer of type I collagen. Following cancer cell inoculation, tumor cells extravasated from the chick vasculature, invaded the surrounding type I collagen-rich extracellular environment and formed nascent tumors over the six day culture period. Ab 770.8 markedly inhibited the ability of MDA-MB-231 cells to form metastatic sites within the surrounding extracellular matrix. Similar, if not identical, results were obtained when Ab 770.8 treatment was delayed for 24 hours after cancer cell inoculation to allow extravasation to proceed to completion. Both Ab 774.3 and Ab 778.17 exhibited the same activity as Ab 770.8 in separate experiments.

The model described in the example is a convenient means to study cancer cell invasion and metastasis, as well as providing a rapid approach for evaluating the ability of potential therapeutics to inhibit these critical processes. The integrin alpha-2 binding agents, Ab 770.8, Ab 774.3 and Ab 778.17, exerted a potent, post-extravasation anti-metastatic activity in vivo.

Example 4

This example describes an additional exemplary in vivo assay for evaluating anti-cancer activity of an integrin alpha-2 binding agent. As detailed below, an integrin alpha-2 binding agent of the invention blocks tumor expansion in collagen-rich environments in vitro and in vivo while displaying inhibitory effects on bony metastases and their sequelae.

To further explore activity in vivo, a mouse bone metastasis model was utilized wherein human breast cancer MDA-MB-231 cells are injected into the left cardiac ventricle. Cells introduced in this manner tend to form metastases in the hindlimb and mandible (Canon et al., 2010; Canon et al., 2008). Following confirmation of successful intracardiac delivery, mice were treated with twice weekly dosages of 10 mg/kg Ab 770.8 for 3 weeks ("treatment period") and tumor progression was monitored by luminescent imaging. At the end of the 3 week antibody trial, mice were held another 2 weeks with no further mAb treatment ("no treatment period").

Treatment with Ab 770.8 had no effect on hindlimb tumor progression, but demonstrated an effect on hindlimb paralysis, a common manifestation of spinal nerve damage secondary to vertebral collapse (Canon et al., *Bone* 46, 1613-1619 (2010); Canon et al., *Clin Exp Metastasis* 25, 119-129 (2008)). During the course of the experiment, it was necessary to euthanize 30% of the control animals by the start of week 4 (i.e., 5 of 15 mice), with 40% euthanized by week 5 due to hindlimb paralysis. In contrast, none of the Ab 770.8-treated mice displayed paralysis during the 3-week treatment period and only 1 (of 10) animals treated with Ab 770.8 exhibited hindlimb paralysis during the 2-week "no treatment" period. In contrast to the effect observed in the femur, MDA-MB-231 proliferation was strikingly suppressed within the space-restricted mandibular compartment. These studies demonstrate that Ab 770.8 blocks tumor expansion in collagen-rich environments in vitro and in vivo while displaying inhibitory effects on bony metastases and their sequelae.

The data provided herein illustrates the impact of an integrin alpha-2 binding agent (Ab 770.8) on breast carcinoma behavior in vivo. Virtually all carcinoma cell types, however, express integrin α2β1 following invasion into surrounding tissues (e.g., ovarian, pancreatic, prostate, colon), supporting a more global role for integrin alpha-2 binding agents as cancer therapeutics (Grzesiak et al., 2007; Kirkland, 2009; Shield et al., 2007; Van Slambrouck et al., 2009; Yoshimura et al., 2009).

Example 5

This example describes an assay for characterizing epitope binding by integrin alpha-2 binding agents. As detailed below, Ab 770.8, Ab 774.3, and Ab 778.17 bind epitopes on the I domain of the alpha-2 integrin at the junction of beta sheet βC and βF within the alpha-2 integrin I domain.

Epitope mapping was performed by incubating monoclonal antibody (mAb) samples with a peptide microarray, followed by incubation with a fluorescent-labelled secondary antibody. After washing, the microarray was scanned in a high-resolution scanning system. The peptide microarray consisted of a set of 15-mer peptides overlapping by 10 residues taken from the human alpha-2 integrin subunit (Genbank accession number AAM34795.1; amino acid residues 1-1133 were used). Peptide arrays, antibody incubations, scanning and data analysis were generated by ProImmune Inc, 4281 Express Lane, Suite L2378, Sarasota, Fla. 34238.

Peptides comprising the amino acid sequence of SEQ ID NO: 32 (YANNPRVVFNLNTYK) and SEQ ID NO: 33 (AIASIPTERYFFNVS) were recognized by Ab 770.8, Ab 774.3, and Ab 778.17. These peptides map to the I domain of the alpha-2 integrin and further comprise the junction of beta sheet βC and βF within the alpha-2 integrin I domain crystal structure. The I domain of integrin alpha-2 interacts with type 1 collagen found in the extracellular matrix. Without wishing to be bound by any particular theory or mechanism of action, binding of Ab 770.8, Ab 774.3, and Ab 778.17 to this region likely disrupts the interaction of integrin alpha-2 and type 1 collagen.

This example describes a method of determining the integrin target region bound by an integrin alpha-2 binding agent. The examiner further describes epitopes recognized by three representative integrin alpha-2 binding agents having anti-cancer activity.

What is claimed is:

1. An anti-integrin alpha-2 antibody or fragment thereof comprising three heavy chain CDRs, CDR-H1, CDR-H2 and CDR-H3 wherein (a) CDR-H1 is SEQ ID NO: 1, CDR-H2 is SEQ ID NO: 2, and CDR-H3 is SEQ ID NO: 3, (b) CDR-H1 is SEQ ID NO: 7, CDR-H2 is SEQ ID NO: 8, and CDR-H3 is SEQ ID NO: 9, or (c) CDR-H1 is SEQ ID NO: 13, CDR-H2 is SEQ ID NO: 14, and CDR-H3 is SEQ ID NO: 15, and three light chain CDRs, CDR-L1, CDR-L2 and CDR-L3 wherein (a) CDR-L1 is SEQ ID NO: 4, CDR-L2 is SEQ ID NO: 5, and CDR-L3 is SEQ ID NO: 6, (b) CDR-L1 is SEQ ID NO: 10, CDR-L2 is SEQ ID NO: 11, and CDR-L3 is SEQ ID NO: 12, or (c) CDR-L1 is SEQ ID NO: 16, CDR-L2 is SEQ ID NO: 17, and CDR-L3 is SEQ ID NO: 18.

2. The anti-integrin alpha-2 antibody or fragment thereof of claim 1, wherein:
   (a) CDR-H1 is SEQ ID NO: 1, CDR-H2 is SEQ ID NO: 2, CDR-H3 is SEQ ID NO: 3, CDR-L1 is SEQ ID NO: 4, CDR-L2 is SEQ ID NO: 5 and CDR-L3 is SEQ ID NO: 6;
   (b) CDR-H1 is SEQ ID NO: 7, CDR-H2 is SEQ ID NO: 8, CDR-H3 is SEQ ID NO: 9, CDR-L1 is SEQ ID NO: 10, CDR-L2 is SEQ ID NO: 11 and CDR-L3 is SEQ ID NO: 12; or
   (c) CDR-H1 is SEQ ID NO: 13, CDR-H2 is SEQ ID NO: 14, CDR-H3 is SEQ ID NO: 15, CDR-L1 is SEQ ID NO: 16, CDR-L2 is SEQ ID NO: 17 and CDR-L3 is SEQ ID NO: 18.

3. The anti-integrin alpha-2 antibody or fragment thereof of claim 1 which is an immunoglobulin comprising heavy and light chains.

4. The anti-integrin alpha-2 antibody or fragment thereof of claim 1, wherein the antibody is a monoclonal antibody.

5. The anti-integrin alpha-2 antibody or fragment thereof of claim 1, which is a chimeric antibody, a humanized antibody, or a human antibody.

6. The anti-integrin alpha-2 antibody or fragment thereof of claim 1, which comprises an F(ab')2, Fab, Fab', Fv, Fc, or Fd fragment.

7. The anti-integrin alpha-2 antibody or fragment thereof of claim 1 comprising:
   (a) heavy chain comprising a polypeptide having the sequence provided in SEQ ID NO: 19, and light chain comprising a polypeptide having the sequence provided in SEQ ID NO: 20;
   (b) heavy chain comprising a polypeptide having the sequence provided in SEQ ID NO: 21, and light chain comprising a polypeptide having the sequence provided in SEQ ID NO: 22; or
   (c) heavy chain comprising a polypeptide having the sequence provided in SEQ ID NO: 23, and light chain comprising a polypeptide having the sequence provided in SEQ ID NO: 24.

8. The anti-integrin alpha-2 antibody or fragment thereof of claim 1, wherein the anti-integrin alpha-2 antibody or fragment thereof inhibits proliferation of cancer cells in a three-dimensional cell culture when the antibody or fragment thereof is present at a concentration of about 50 nM to about 500 nM.

9. A process for the production of an anti-integrin alpha-2 antibody or fragment thereof, comprising culturing a host cell expressing the anti-integrin alpha-2 antibody or fragment thereof of claim 1 and isolating the anti-integrin alpha-2 antibody or fragment thereof.

10. A pharmaceutical composition comprising an anti-integrin alpha-2 antibody or fragment thereof of claim 1 in combination with one or more of a pharmaceutically acceptable excipient, diluent or carrier.

* * * * *

SEQUENCE LISTING

```
<160> NUMBER OF SEQ ID NOS: 33

<210> SEQ ID NO 1
<211> LENGTH: 8
<212> TYPE: PRT
<213> ORGANISM: Mus musculus

<400> SEQUENCE: 1

Gly Tyr Ser Phe Thr Ser Tyr Trp
1               5

<210> SEQ ID NO 2
<211> LENGTH: 8
<212> TYPE: PRT
<213> ORGANISM: Mus musculus

<400> SEQUENCE: 2

Phe Tyr Pro Gly Asn Ser Glu Asp
1               5
```

<210> SEQ ID NO 3
<211> LENGTH: 13
<212> TYPE: PRT
<213> ORGANISM: Mus musculus

<400> SEQUENCE: 3

Thr Arg Gly Thr Thr Leu Val Ala Pro Gly Phe Asp Val
1               5                   10

<210> SEQ ID NO 4
<211> LENGTH: 6
<212> TYPE: PRT
<213> ORGANISM: Mus musculus

<400> SEQUENCE: 4

Gln Ser Ile Gly Thr Ser
1               5

<210> SEQ ID NO 5
<211> LENGTH: 3
<212> TYPE: PRT
<213> ORGANISM: Mus musculus

<400> SEQUENCE: 5

Tyr Val Ser
1

<210> SEQ ID NO 6
<211> LENGTH: 9
<212> TYPE: PRT
<213> ORGANISM: Mus musculus

<400> SEQUENCE: 6

Gln His Ser Asn Arg Trp Pro Leu Thr
1               5

<210> SEQ ID NO 7
<211> LENGTH: 8
<212> TYPE: PRT
<213> ORGANISM: Mus musculus

<400> SEQUENCE: 7

Gly Tyr Thr Phe Ala Ser Tyr Trp
1               5

<210> SEQ ID NO 8
<211> LENGTH: 8
<212> TYPE: PRT
<213> ORGANISM: Mus musculus

<400> SEQUENCE: 8

Ile Asp Pro Tyr Asp Ser Glu Thr
1               5

<210> SEQ ID NO 9
<211> LENGTH: 10
<212> TYPE: PRT
<213> ORGANISM: Mus musculus

<400> SEQUENCE: 9

Ala Arg Leu Gly Arg Gly Pro Phe Ala Tyr
1               5                   10

```
<210> SEQ ID NO 10
<211> LENGTH: 10
<212> TYPE: PRT
<213> ORGANISM: Mus musculus

<400> SEQUENCE: 10

Glu Ser Val Asp Ser Tyr Asp Asn Ser Phe
1               5                   10

<210> SEQ ID NO 11
<211> LENGTH: 3
<212> TYPE: PRT
<213> ORGANISM: Mus musculus

<400> SEQUENCE: 11

Phe Ala Ser
1

<210> SEQ ID NO 12
<211> LENGTH: 9
<212> TYPE: PRT
<213> ORGANISM: Mus musculus

<400> SEQUENCE: 12

Gln Gln Asn Asn Glu Asp Pro Tyr Thr
1               5

<210> SEQ ID NO 13
<211> LENGTH: 8
<212> TYPE: PRT
<213> ORGANISM: Mus musculus

<400> SEQUENCE: 13

Gly Leu Ser Leu Thr Asn Tyr Gly
1               5

<210> SEQ ID NO 14
<211> LENGTH: 7
<212> TYPE: PRT
<213> ORGANISM: Mus musculus

<400> SEQUENCE: 14

Ile Trp Ser Gly Gly Asn Thr
1               5

<210> SEQ ID NO 15
<211> LENGTH: 6
<212> TYPE: PRT
<213> ORGANISM: Mus musculus

<400> SEQUENCE: 15

Leu Ser His Arg Leu Leu
1               5

<210> SEQ ID NO 16
<211> LENGTH: 6
<212> TYPE: PRT
<213> ORGANISM: Mus musculus

<400> SEQUENCE: 16

Gln Asp Val Gly Thr Ala
1               5

<210> SEQ ID NO 17
<211> LENGTH: 3
```

```
<212> TYPE: PRT
<213> ORGANISM: Mus musculus

<400> SEQUENCE: 17

Trp Ala Ala
1

<210> SEQ ID NO 18
<211> LENGTH: 9
<212> TYPE: PRT
<213> ORGANISM: Mus musculus

<400> SEQUENCE: 18

Gln Gln Tyr Ser Thr Tyr Pro Leu Thr
1               5

<210> SEQ ID NO 19
<211> LENGTH: 133
<212> TYPE: PRT
<213> ORGANISM: Mus musculus

<400> SEQUENCE: 19

Glu Val Lys Leu Glu Glu Ser Gly Thr Val Leu Ala Arg Pro Gly Ala
1               5                   10                  15

Ser Val Lys Met Ser Cys Lys Ala Ser Gly Tyr Ser Phe Thr Ser Tyr
                20                  25                  30

Trp Met His Trp Val Lys Gln Arg Pro Gly Gln Gly Leu Glu Trp Ile
            35                  40                  45

Gly Ala Phe Tyr Pro Gly Asn Ser Glu Asp Lys Tyr Asn Glu Asn Phe
        50                  55                  60

Lys Ile Lys Ala Lys Leu Thr Ala Val Thr Ser Val Asn Thr Val Tyr
65                  70                  75                  80

Met Glu Leu Ser Ser Leu Thr Ser Glu Asp Ser Ala Val Tyr Tyr Cys
                85                  90                  95

Thr Arg Gly Thr Thr Leu Val Ala Pro Gly Phe Asp Val Trp Gly Ala
            100                 105                 110

Gly Thr Thr Val Thr Val Ser Ser Ala Lys Thr Thr Pro Pro Ser Val
        115                 120                 125

Tyr Pro Leu Val Pro
        130

<210> SEQ ID NO 20
<211> LENGTH: 116
<212> TYPE: PRT
<213> ORGANISM: Mus musculus

<400> SEQUENCE: 20

Asp Ile Val Met Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Ser
                20                  25                  30

Ile His Trp Tyr Gln Gln Arg Thr Asn Gly Ser Pro Arg Leu Leu Ile
            35                  40                  45

Lys Tyr Val Ser Glu Ser Ile Ser Gly Ile Pro Ser Arg Phe Ser Gly
        50                  55                  60

Ser Gly Ser Gly Thr Asp Phe Thr Leu Thr Ile Asn Ser Val Glu Ser
65                  70                  75                  80

Glu Asp Ile Ala Asp Tyr Tyr Cys Gln His Ser Asn Arg Trp Pro Leu
                85                  90                  95
```

```
Thr Phe Gly Ala Gly Thr Lys Leu Glu Leu Lys Arg Ala Asp Ala Ala
                100                 105                 110

Pro Thr Val Ser
        115

<210> SEQ ID NO 21
<211> LENGTH: 126
<212> TYPE: PRT
<213> ORGANISM: Mus musculus

<400> SEQUENCE: 21

Gln Val Gln Leu Gln Gln Pro Gly Ala Glu Leu Val Arg Pro Gly Thr
1               5                   10                  15

Ser Val Lys Leu Ser Cys Lys Ala Ser Gly Tyr Thr Phe Ala Ser Tyr
            20                  25                  30

Trp Met Asn Trp Val Ser Gln Arg Pro Glu Gln Gly Leu Glu Trp Ile
        35                  40                  45

Gly Arg Ile Asp Pro Tyr Asp Ser Glu Thr His Tyr Asn Gln Lys Phe
    50                  55                  60

Lys Asp Lys Ala Ile Leu Thr Val Asp Lys Ser Ser Thr Ala Tyr
65                  70                  75                  80

Ile Gln Leu Asn Ser Leu Thr Ser Glu Asp Ser Ala Val Tyr Tyr Cys
                85                  90                  95

Ala Arg Leu Gly Arg Gly Pro Phe Ala Tyr Trp Gly Gln Gly Thr Leu
                100                 105                 110

Val Thr Val Ser Ala Ala Lys Thr Thr Pro Pro Ser Val Tyr
            115                 120                 125

<210> SEQ ID NO 22
<211> LENGTH: 120
<212> TYPE: PRT
<213> ORGANISM: Mus musculus

<400> SEQUENCE: 22

Asp Ile Val Met Thr Gln Thr Pro Thr Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Asp Asn Ser Phe Met Tyr Trp Tyr Gln Gln Lys Pro Gly Gln Pro Pro
        35                  40                  45

Lys Leu Leu Ile Tyr Phe Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Asn
                85                  90                  95

Glu Asp Pro Tyr Thr Phe Gly Gly Thr Lys Leu Glu Ile Lys Arg
                100                 105                 110

Ala Asp Ala Ala Pro Thr Val Ser
            115                 120

<210> SEQ ID NO 23
<211> LENGTH: 109
<212> TYPE: PRT
<213> ORGANISM: Mus musculus

<400> SEQUENCE: 23
```

```
Glu Val Gln Leu Gln Glu Ser Gly Pro Gly Leu Val Gln Pro Ser Gln
1               5                   10                  15

Ser Leu Ser Ile Thr Cys Thr Val Ser Gly Leu Ser Leu Thr Asn Tyr
            20                  25                  30

Gly Val His Trp Val Arg Gln Ser Pro Gly Lys Gly Leu Glu Trp Leu
            35                  40                  45

Gly Val Ile Trp Ser Gly Gly Asn Thr Asp Tyr Asn Ala Ala Phe Ile
50                  55                  60

Ser Arg Leu Asn Ile Lys Lys Asp Asn Ser Lys Asn Gln Val Phe Phe
65                  70                  75                  80

Lys Met Asn Ser Leu Gln Val Asn Asp Thr Val Gly Ser Arg Asn Leu
                85                  90                  95

Ser His Arg Leu Leu Arg Glu Ser Val Leu Pro Lys Cys
            100                 105
```

<210> SEQ ID NO 24
<211> LENGTH: 102
<212> TYPE: PRT
<213> ORGANISM: Mus musculus

<400> SEQUENCE: 24

```
Gly Tyr Ser Trp Cys Ser Ile Thr Cys Lys Ala Ser Gln Asp Val Gly
1               5                   10                  15

Thr Ala Val Ala Trp Tyr Gln Gln Lys Pro Gly Gln Ser Pro Lys Leu
            20                  25                  30

Leu Ile Tyr Trp Ala Ala Thr Arg His Thr Gly Val Pro Asp Arg Phe
            35                  40                  45

Ala Gly Ser Gly Ser Gly Thr Asp Phe Thr Leu Thr Ile Ser Asn Val
50                  55                  60

Gln Ser Glu Asp Leu Ala Asp Tyr Phe Cys Gln Gln Tyr Ser Thr Tyr
65                  70                  75                  80

Pro Leu Thr Phe Gly Ala Gly Thr Lys Leu Glu Leu Lys Arg Ala Asp
                85                  90                  95

Ala Ala Pro Thr Val Ser
            100
```

<210> SEQ ID NO 25
<211> LENGTH: 1181
<212> TYPE: PRT
<213> ORGANISM: Homo sapiens

<400> SEQUENCE: 25

```
Met Gly Pro Glu Arg Thr Gly Ala Ala Pro Leu Pro Leu Leu Leu Val
1               5                   10                  15

Leu Ala Leu Ser Gln Gly Ile Leu Asn Cys Cys Leu Ala Tyr Asn Val
            20                  25                  30

Gly Leu Pro Glu Ala Lys Ile Phe Ser Gly Pro Ser Ser Glu Gln Phe
            35                  40                  45

Gly Tyr Ala Val Gln Gln Phe Ile Asn Pro Lys Gly Asn Trp Leu Leu
50                  55                  60

Val Gly Ser Pro Trp Ser Gly Phe Pro Glu Asn Arg Met Gly Asp Val
65                  70                  75                  80

Tyr Lys Cys Pro Val Asp Leu Ser Thr Ala Thr Cys Glu Lys Leu Asn
                85                  90                  95

Leu Gln Thr Ser Thr Ser Ile Pro Asn Val Thr Glu Met Lys Thr Asn
            100                 105                 110
```

```
Met Ser Leu Gly Leu Ile Leu Thr Arg Asn Met Gly Thr Gly Gly Phe
            115                 120                 125
Leu Thr Cys Gly Pro Leu Trp Ala Gln Gln Cys Gly Asn Gln Tyr Tyr
        130                 135                 140
Thr Thr Gly Val Cys Ser Asp Ile Ser Pro Asp Phe Gln Leu Ser Ala
145                 150                 155                 160
Ser Phe Ser Pro Ala Thr Gln Pro Cys Pro Ser Leu Ile Asp Val Val
                165                 170                 175
Val Val Cys Asp Glu Ser Asn Ser Ile Tyr Pro Trp Asp Ala Val Lys
            180                 185                 190
Asn Phe Leu Glu Lys Phe Val Gln Gly Leu Asp Ile Gly Pro Thr Lys
        195                 200                 205
Thr Gln Val Gly Leu Ile Gln Tyr Ala Asn Asn Pro Arg Val Val Phe
    210                 215                 220
Asn Leu Asn Thr Tyr Lys Thr Lys Glu Glu Met Ile Val Ala Thr Ser
225                 230                 235                 240
Gln Thr Ser Gln Tyr Gly Gly Asp Leu Thr Asn Thr Phe Gly Ala Ile
                245                 250                 255
Gln Tyr Ala Arg Lys Tyr Ala Tyr Ser Ala Ala Ser Gly Gly Arg Arg
            260                 265                 270
Ser Ala Thr Lys Val Met Val Val Val Thr Asp Gly Glu Ser His Asp
        275                 280                 285
Gly Ser Met Leu Lys Ala Val Ile Asp Gln Cys Asn His Asp Asn Ile
    290                 295                 300
Leu Arg Phe Gly Ile Ala Val Leu Gly Tyr Leu Asn Arg Asn Ala Leu
305                 310                 315                 320
Asp Thr Lys Asn Leu Ile Lys Glu Ile Lys Ala Ile Ala Ser Ile Pro
                325                 330                 335
Thr Glu Arg Tyr Phe Phe Asn Val Ser Asp Glu Ala Ala Leu Leu Glu
            340                 345                 350
Lys Ala Gly Thr Leu Gly Glu Gln Ile Phe Ser Ile Glu Gly Thr Val
        355                 360                 365
Gln Gly Gly Asp Asn Phe Gln Met Glu Met Ser Gln Val Gly Phe Ser
    370                 375                 380
Ala Asp Tyr Ser Ser Gln Asn Asp Ile Leu Met Leu Gly Ala Val Gly
385                 390                 395                 400
Ala Phe Gly Trp Ser Gly Thr Ile Val Gln Lys Thr Ser His Gly His
                405                 410                 415
Leu Ile Phe Pro Lys Gln Ala Phe Asp Gln Ile Leu Gln Asp Arg Asn
            420                 425                 430
His Ser Ser Tyr Leu Gly Tyr Ser Val Ala Ala Ile Ser Thr Gly Glu
        435                 440                 445
Ser Thr His Phe Val Ala Gly Ala Pro Arg Ala Asn Tyr Thr Gly Gln
    450                 455                 460
Ile Val Leu Tyr Ser Val Asn Glu Asn Gly Asn Ile Thr Val Ile Gln
465                 470                 475                 480
Ala His Arg Gly Asp Gln Ile Gly Ser Tyr Phe Gly Ser Val Leu Cys
                485                 490                 495
Ser Val Asp Val Asp Lys Asp Thr Ile Thr Asp Val Leu Leu Val Gly
            500                 505                 510
Ala Pro Met Tyr Met Ser Asp Leu Lys Lys Glu Glu Gly Arg Val Tyr
        515                 520                 525
Leu Phe Thr Ile Lys Glu Gly Ile Leu Gly Gln His Gln Phe Leu Glu
```

```
                530               535               540
Gly Pro Glu Gly Ile Glu Asn Thr Arg Phe Gly Ser Ala Ile Ala Ala
545               550               555               560

Leu Ser Asp Ile Asn Met Asp Gly Phe Asn Asp Val Ile Val Gly Ser
                565               570               575

Pro Leu Glu Asn Gln Asn Ser Gly Ala Val Tyr Ile Tyr Asn Gly His
                580               585               590

Gln Gly Thr Ile Arg Thr Lys Tyr Ser Gln Lys Ile Leu Gly Ser Asp
            595               600               605

Gly Ala Phe Arg Ser His Leu Gln Tyr Phe Gly Arg Ser Leu Asp Gly
        610               615               620

Tyr Gly Asp Leu Asn Gly Asp Ser Ile Thr Asp Val Ser Ile Gly Ala
625               630               635               640

Phe Gly Gln Val Val Gln Leu Trp Ser Gln Ser Ile Ala Asp Val Ala
                645               650               655

Ile Glu Ala Ser Phe Thr Pro Glu Lys Ile Thr Leu Val Asn Lys Asn
                660               665               670

Ala Gln Ile Ile Leu Lys Leu Cys Phe Ser Ala Lys Phe Arg Pro Thr
            675               680               685

Lys Gln Asn Asn Gln Val Ala Ile Val Tyr Asn Ile Thr Leu Asp Ala
        690               695               700

Asp Gly Phe Ser Ser Arg Val Thr Ser Arg Gly Leu Phe Lys Glu Asn
705               710               715               720

Asn Glu Arg Cys Leu Gln Lys Asn Met Val Val Asn Gln Ala Gln Ser
                725               730               735

Cys Pro Glu His Ile Ile Tyr Ile Gln Glu Pro Ser Asp Val Val Asn
                740               745               750

Ser Leu Asp Leu Arg Val Asp Ile Ser Leu Glu Asn Pro Gly Thr Ser
            755               760               765

Pro Ala Leu Glu Ala Tyr Ser Glu Thr Ala Lys Val Phe Ser Ile Pro
        770               775               780

Phe His Lys Asp Cys Gly Glu Asp Gly Leu Cys Ile Ser Asp Leu Val
785               790               795               800

Leu Asp Val Arg Gln Ile Pro Ala Ala Gln Glu Gln Pro Phe Ile Val
                805               810               815

Ser Asn Gln Asn Lys Arg Leu Thr Phe Ser Val Thr Leu Lys Asn Lys
                820               825               830

Arg Glu Ser Ala Tyr Asn Thr Gly Ile Val Val Asp Phe Ser Glu Asn
            835               840               845

Leu Phe Phe Ala Ser Phe Ser Leu Pro Val Asp Gly Thr Glu Val Thr
        850               855               860

Cys Gln Val Ala Ala Ser Gln Lys Ser Val Ala Cys Asp Val Gly Tyr
865               870               875               880

Pro Ala Leu Lys Arg Glu Gln Gln Val Thr Phe Thr Ile Asn Phe Asp
                885               890               895

Phe Asn Leu Gln Asn Leu Gln Asn Gln Ala Ser Leu Ser Phe Gln Ala
                900               905               910

Leu Ser Glu Ser Gln Glu Glu Asn Lys Ala Asp Asn Leu Val Asn Leu
            915               920               925

Lys Ile Pro Leu Leu Tyr Asp Ala Glu Ile His Leu Thr Arg Ser Thr
        930               935               940

Asn Ile Asn Phe Tyr Glu Ile Ser Ser Asp Gly Asn Val Pro Ser Ile
945               950               955               960
```

Val His Ser Phe Glu Asp Val Gly Pro Lys Phe Ile Phe Ser Leu Lys
            965                 970                 975

Val Thr Thr Gly Ser Val Pro Val Ser Met Ala Thr Val Ile Ile His
            980                 985                 990

Ile Pro Gln Tyr Thr Lys Glu Lys Asn Pro Leu Met Tyr Leu Thr Gly
            995                 1000                1005

Val Gln Thr Asp Lys Ala Gly Asp Ile Ser Cys Asn Ala Asp Ile
        1010                1015                1020

Asn Pro Leu Lys Ile Gly Gln Thr Ser Ser Val Ser Phe Lys
        1025                1030                1035

Ser Glu Asn Phe Arg His Thr Lys Glu Leu Asn Cys Arg Thr Ala
        1040                1045                1050

Ser Cys Ser Asn Val Thr Cys Trp Leu Lys Asp Val His Met Lys
        1055                1060                1065

Gly Glu Tyr Phe Val Asn Val Thr Thr Arg Ile Trp Asn Gly Thr
        1070                1075                1080

Phe Ala Ser Ser Thr Phe Gln Thr Val Gln Leu Thr Ala Ala Ala
        1085                1090                1095

Glu Ile Asn Thr Tyr Asn Pro Glu Ile Tyr Val Ile Glu Asp Asn
        1100                1105                1110

Thr Val Thr Ile Pro Leu Met Ile Met Lys Pro Asp Glu Lys Ala
        1115                1120                1125

Glu Val Pro Thr Gly Val Ile Ile Gly Ser Ile Ile Ala Gly Ile
        1130                1135                1140

Leu Leu Leu Leu Ala Leu Val Ala Ile Leu Trp Lys Leu Gly Phe
        1145                1150                1155

Phe Lys Arg Lys Tyr Glu Lys Met Thr Lys Asn Pro Asp Glu Ile
        1160                1165                1170

Asp Glu Thr Thr Glu Leu Ser Ser
        1175                1180

<210> SEQ ID NO 26
<211> LENGTH: 399
<212> TYPE: DNA
<213> ORGANISM: Mus musculus

<400> SEQUENCE: 26
gaagtgaagc tggaggagtc agggactgtg ctggcaaggc ctggggcttc cgtgaagatg    60
tcctgcaagg cttctggcta cagttttact agctattgga tgcactgggt aaaacagagg   120
cctggacagg gtctagaatg gattggtgct ttttatcctg gaaatagtga agataaatat   180
aacgagaatt tcaagatcaa ggccaaactg actgcagtca catccgtcaa tactgtctac   240
atggagctca gcagcctgac aagtgaggac tctgcggtct attattgtac aagagggact   300
acgttagtag ctccgggctt cgatgtctgg ggcgcaggga ctacggtcac cgtctcctca   360
gccaaaacga caccccccatc tgtctatccc ttggtccct                         399

<210> SEQ ID NO 27
<211> LENGTH: 348
<212> TYPE: DNA
<213> ORGANISM: Mus musculus

<400> SEQUENCE: 27
gatattgtga tgacacaatc tccagccatc ctgtctgtga gtccaggaga aagagtcagt    60
ttctcctgca gggccagtca gagcattggc acaagcatac actggtatca gcaagaaca   120

```
aatggttctc caaggcttct cataaagtat gtttctgagt ctatctctgg gatcccttcc    180
aggtttagtg gcagtggatc agggacagat tttactctta ccatcaacag tgtggagtct    240
gaagatattg cagattatta ctgtcaacac agtaataggt ggccgctcac gttcggtgct    300
gggaccaagc tggagctgaa acgggctgat gctgcaccaa ctgtatcc                 348
```

<210> SEQ ID NO 28
<211> LENGTH: 378
<212> TYPE: DNA
<213> ORGANISM: Mus musculus

<400> SEQUENCE: 28

```
caggtccaac tacagcagcc tggggctgaa ctggtgaggc ctgggacttc agtgaagctg    60
tcctgcaagg cttctggcta cacgttcgcc agctactgga tgaactgggt tagtcagagg    120
cctgagcaag gccttgagtg gattggaagg atcgatcctt acgatagtga aactcactac    180
aatcaaaagt tcaaggacaa ggccatattg actgtagaca atcctccag cacagcctac     240 atacaactca acagcctgac atctgaggac tctgcggtct attactgtgc aagattaggg    300 aggggggcctt ttgcttactg gggccaaggg actctggtca ctgtctctgc agccaaaacg   360 acaccccat ctgtctat                                                    378
```

<210> SEQ ID NO 29
<211> LENGTH: 360
<212> TYPE: DNA
<213> ORGANISM: Mus musculus

<400> SEQUENCE: 29

```
gatattgtga tgacccagac tccaacttct ttggctgtgt ctctagggca gagggccacc    60
atatcctgca gagccagtga agtgttgat agttatgaca cagttttat gtattggtac      120 cagcagaaac caggacagcc acccaaactc ctcatctatt ttgcatccaa cctagaatct    180
ggggtccctg ccaggttcag tggcagtggg tctaggacag acttcaccct caccattgat    240
cctgtggagg ctgatgatgc tgcaacctat tactgtcagc aaaataatga ggatccgtac    300
acgttcggag gggggaccaa gctggaaata aaacgggctg atgctgcacc aactgtatcc    360
```

<210> SEQ ID NO 30
<211> LENGTH: 327
<212> TYPE: DNA
<213> ORGANISM: Mus musculus

<400> SEQUENCE: 30

```
gaggtacagc tgcaggagtc aggacctggc ctagtgcagc cctcacagag cctgtccatc    60
acctgcacag tctctggttt gtcattaact aattatggtg tccactgggt tcgccagtct    120
ccaggaaagg gtctggagtg gctgggagtg atttggagtg gtggaaacac agactataac    180
gcagctttca tatccagact gaacatcaag aaggacaatt ccaagaacca agtcttcttt    240
aaaatgaaca gtctgcaagt taatgacaca gtcgggtcaa ggaacctcag tcaccgtctc    300
ctcagagagt cagtccttcc caaatgt                                        327
```

<210> SEQ ID NO 31
<211> LENGTH: 306
<212> TYPE: DNA
<213> ORGANISM: Mus musculus

<400> SEQUENCE: 31

```
ggatacagtt ggtgcagcat cacctgcaag gccagtcagg atgtgggtac tgctgtcgcc    60
tggtatcaac agaaaccagg gcaatctcct aaattactga tttactgggc agccacccgg   120
cacactggag tccctgatcg cttcgcaggc agtggatctg ggacagactt cactctcacc   180
attagcaatg tgcagtctga agacttggca gattatttct gtcaacaata tgcacctat   240 ccactcacgt tcggtgctgg gaccaagctg gagctgaaac gggctgatgc tgcaccaact   300
gtatcc                                                               306
```

```
<210> SEQ ID NO 32
<211> LENGTH: 15
<212> TYPE: PRT
<213> ORGANISM: Homo sapiens

<400> SEQUENCE: 32

Tyr Ala Asn Asn Pro Arg Val Val Phe Asn Leu Asn Thr Tyr Lys
1               5                   10                  15

<210> SEQ ID NO 33
<211> LENGTH: 15
<212> TYPE: PRT
<213> ORGANISM: Homo sapiens

<400> SEQUENCE: 33

Ala Ile Ala Ser Ile Pro Thr Glu Arg Tyr Phe Phe Asn Val Ser
1               5                   10                  15
```